(12) United States Patent
Weissleder et al.

(10) Patent No.: US 10,724,948 B2
(45) Date of Patent: *Jul. 28, 2020

(54) PORTABLE DIFFRACTION-BASED IMAGING AND DIAGNOSTIC SYSTEMS AND METHODS

(71) Applicant: The General Hospital Corporation, Boston, MA (US)

(72) Inventors: Ralph Weissleder, Peabody, MA (US); Hakho Lee, Acton, MA (US); Hyungsoon Im, Peabody, MA (US); Cesar Castro, Reading, MA (US)

(73) Assignee: The General Hospital Corporation, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/025,615

(22) Filed: Jul. 2, 2018

(65) Prior Publication Data

US 2019/0113451 A1 Apr. 18, 2019

Related U.S. Application Data

(63) Continuation of application No. 14/912,038, filed as application No. PCT/US2014/051522 on Aug. 18, 2014, now Pat. No. 10,012,589.

(Continued)

(51) Int. Cl.
*G01N 21/47* (2006.01)
*G01N 15/02* (2006.01)
(Continued)

(52) U.S. Cl.
CPC ......... *G01N 21/4788* (2013.01); *C12Q 1/708* (2013.01); *G01N 15/0211* (2013.01);
(Continued)

(58) Field of Classification Search
CPC ........... G01N 15/0612; G01N 15/0227; G01N 15/06; G01N 15/0211; G01N 21/4788;
(Continued)

(56) References Cited

U.S. PATENT DOCUMENTS 4,213,036 A 7/1980 Kopp
4,621,063 A 11/1986 Wyatt
(Continued)

FOREIGN PATENT DOCUMENTS

WO WO 2010/042555 4/2010
WO WO 2012/047653 4/2012

OTHER PUBLICATIONS

Akakin et al., "Content-based microscopic image retrieval system for multi-image queries," IEEE Trans. Inf. Technol. Biomed., Jul. 2012, 16(4): 758-769.

(Continued)

*Primary Examiner* — John B Strege
(74) *Attorney, Agent, or Firm* — Fish & Richardson P.C.

(57) ABSTRACT

The disclosure features systems and methods for measuring and diagnosing target constituents bound to labeling particles in a sample. The systems include a radiation source, a sample holder, a detector configured to obtain one or more diffraction patterns of the sample each including information corresponding to optical properties of sample constituents, and an electronic processor configured to, for each of the one or more diffraction patterns: (a) analyze the diffraction pattern to obtain amplitude information and phase information corresponding to the sample constituents; (b) identify one or more particle-bound target sample constituents based on at least one of the amplitude information and the phase information; and (c) determine an amount of at least one of (Continued)

the particle-bound target sample constituents in the sample based on at least one of the amplitude information and the phase information.

21 Claims, 21 Drawing Sheets

Related U.S. Application Data

(60) Provisional application No. 61/867,015, filed on Aug. 16, 2013.

(51) Int. Cl.
| | |
|---|---|
| *G01N 33/574* | (2006.01) |
| *G01N 33/569* | (2006.01) |
| *C12Q 1/70* | (2006.01) |
| *G03H 1/08* | (2006.01) |
| *G03H 1/04* | (2006.01) |
| *G01N 15/06* | (2006.01) |
| *G01N 15/00* | (2006.01) |
| *G01N 15/10* | (2006.01) |
| *G01N 15/14* | (2006.01) |

(52) U.S. Cl.
CPC ......... *G01N 15/0227* (2013.01); *G01N 15/06* (2013.01); *G01N 15/0612* (2013.01); *G01N 33/56972* (2013.01); *G01N 33/57407* (2013.01); *G01N 33/57411* (2013.01); *G03H 1/0443* (2013.01); *G03H 1/0866* (2013.01); *G01N 2015/0065* (2013.01); *G01N 2015/0693* (2013.01); *G01N 2015/1006* (2013.01); *G01N 2015/1486* (2013.01); *G03H 2001/0447* (2013.01)

(58) Field of Classification Search
CPC ....... G01N 33/57407; G01N 33/56972; G01N 33/57411; G01N 2015/0065; G01N 2015/1486; G01N 2015/1006; G01N 2015/0693; C12Q 1/708; G03H 2001/0447
See application file for complete search history.

(56) References Cited

U.S. PATENT DOCUMENTS

| | | | |
|---|---|---|---|
| 5,715,819 A | 2/1998 | Svenson et al. | |
| 7,545,865 B2 | 6/2009 | Bengtson | |
| 10,012,589 B2 * | 7/2018 | Weissleder | G01N 15/0211 |
| 2005/0287604 A1 | 12/2005 | Bohmer | |
| 2006/0078998 A1 | 4/2006 | Puskas et al. | |
| 2006/0204071 A1 | 9/2006 | Ortyn | |
| 2006/0211071 A1 | 9/2006 | Andre | |
| 2007/0278386 A1 | 12/2007 | Paxman et al. | |
| 2009/0105172 A1 | 4/2009 | Diener et al. | |
| 2009/0125242 A1 | 5/2009 | Choi et al. | |
| 2009/0258365 A1 | 10/2009 | Terstappen et al. | |
| 2011/0009163 A1 | 1/2011 | Fletcher et al. | |
| 2012/0248292 A1 | 10/2012 | Ozcan et al. | |
| 2012/0257037 A1 | 10/2012 | Raicu | |
| 2013/0295683 A1 | 11/2013 | Mundill | |
| 2014/0200459 A1 | 7/2014 | Hendriks | |

OTHER PUBLICATIONS

Amador-Ortiz et al., "Combined Core Needle Biopsy and Fine-Needle Aspiration With Ancillary Studies Correlate Highly With Traditional Techniques in the Diagnosis of Nodal-Based Lymphoma," Am. J. Clin. Pathol., 2011,135: 516-524.
Bogusz et al., "Quantitative immunofluorescence reveals the signature of active B-cell receptor signaling in diffuse large B-cell lymphoma," Clin. Cancer Res., Nov. 2012, 18(22): 6122-6135.
Chung et al., "A magneto-DNA nanoparticle system for rapid detection and phenotyping of bacteria," Nature Nanotechnology, May 2013, 8(5): 369-375.
Chung et al., "Microfluidic cell sorter (µFCS) for on-chip capture and analysis of single cells," Adv. Healthcare Mater., Jul. 2012, 1(4): 432-6.
Chung et al., "Rare cell isolation and profiling on a hybrid magnetic/size-sorting chip," Biomicrofluidics, Sep. 2013, RaR7(5): 54107.
Haun et al., "Bioorthogonal chemistry amplifies nanoparticle binding and enhances the sensitivity of cell detection," Nature Nanotechnology, Sep. 2010, 5(9): 660-665.
International Preliminary Report on Patentability in International Application No. PCT/US2014/051522, dated Feb. 16, 2016, 14 pages.
International Search Report and Written Opinion in International Application No. PCT/US2014/051522, dated Dec. 18, 2014, 17 pages.
Jaffe, "The 2008 WHO classification of lymphomas: implications for clinical practice and translational research," Hematology Am. Soc. Hematol. Educ. Program, 2009, 523-531.
Javier et al., "Aptamer-targeted gold nanoparticles as molecular-specific contrast agents for reflectance imaging," Bioconjug Chem, Jun. 2008, 19(6):1309-1312.
LaCasce et al., "Comparison of referring and final pathology for patients with non-Hodgkin's lymphoma in the National Comprehensive Cancer Network," J. Clin. Oncol., Nov. 2008, 26: 5107-5112.
Liong et al., "Magnetic barcode assay for genetic detection of pathogens," Nature Communications, 2013, 4: 1752.
Matasar et al., "Expert second-opinion pathology review of lymphoma in the era of the World Health Organization classification," Ann. Oncol., Jan. 2012, 23: 159-166.
Sau et al., "One-step high-yield aqueous synthesis of size-tunable multispiked gold nanoparticles," Small, Aug. 2011, 7(15): 2188-2194.
Sun et al., "Whole Genome Sequencing and Evolutionary Analysis of Human Papillomavirus Type 16 in Central China," Plos One, 2012, 7(5): e36577.
Swerdlow et al., "The 2016 revision of the World Health Organization classification of lymphoid neoplasms," Blood, May 2016, 127:2375-2390.

* cited by examiner

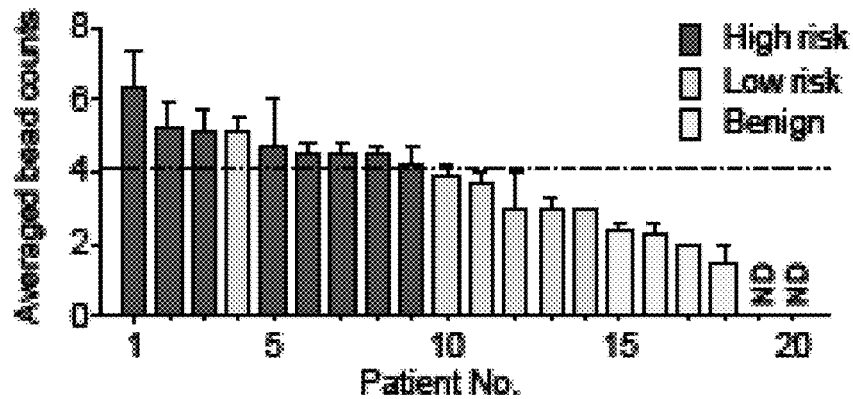
FIG 11B
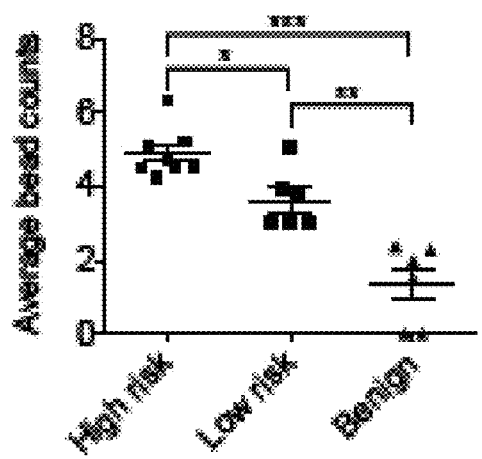 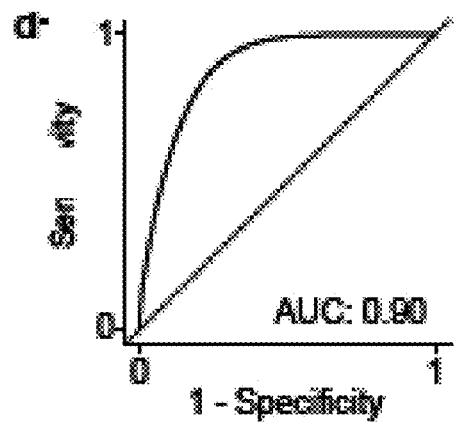
FIG. 11C          FIG. 11D
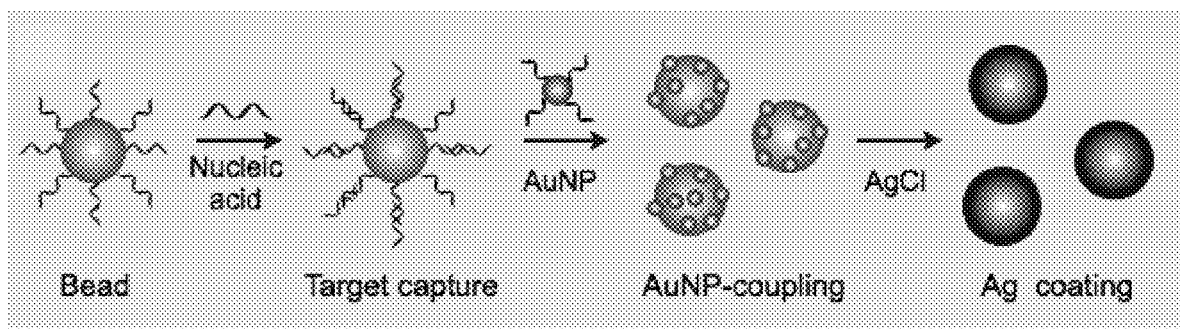
FIG. 11E

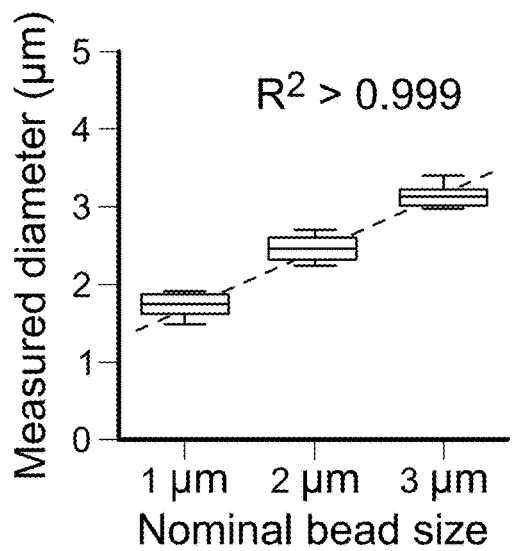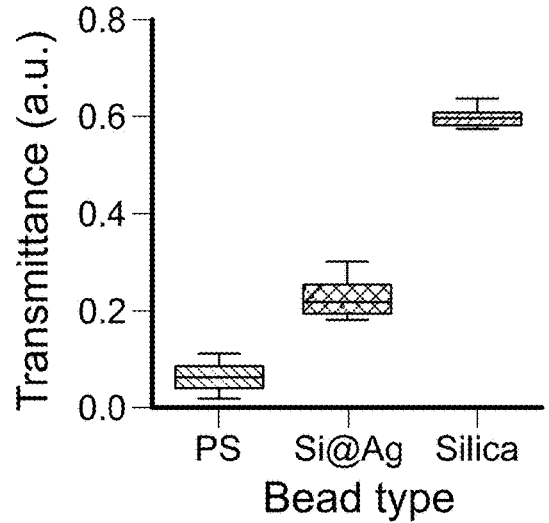
FIG. 12A  FIG. 12B
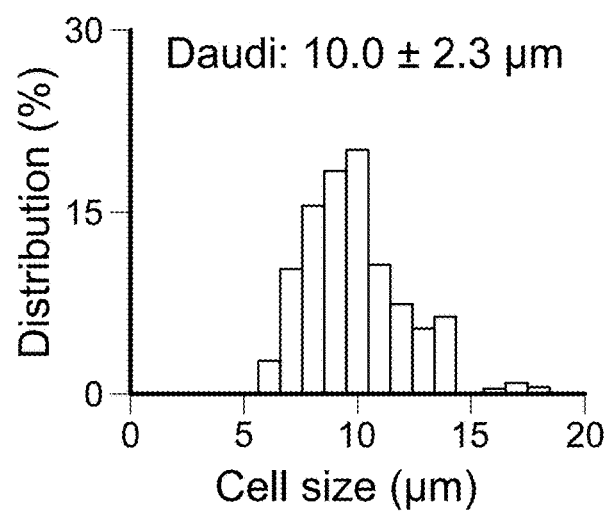
FIG. 12C

PORTABLE DIFFRACTION-BASED IMAGING AND DIAGNOSTIC SYSTEMS AND METHODS

CROSS-REFERENCE TO RELATED APPLICATIONS

This application is a continuation of U.S. patent application Ser. No. 14/912,038, filed Feb. 12, 2016, which is a U.S. National Phase Application under 35 U.S.C. § 371 of International Patent Application No. PCT/US2014/051522, filed on Aug. 18, 2014, which claims priority to U.S. Provisional Patent Application No. 61/867,015, filed on Aug. 16, 2013, the entire contents of which are incorporated by reference herein.

STATEMENT AS TO FEDERALLY SPONSORED RESEARCH

This invention was made with Government support under grant nos. R01EB004626, R01EB010011, HHSN268201000044C, R01HL113156. The Government has certain rights in the invention.

TECHNICAL FIELD

This disclosure relates to diagnostic measurement of biological and other samples.

BACKGROUND

Rare cells, such as circulating tumor cells (CTCs), are found in peripheral blood samples in very low numbers. For example, CTCs in the blood of cancer patients are found in a concentration of less than 100 cells per ml of blood. Because CTCs are known to be shed from a primary tumor and to cause metastasis, rapid detection and identification of these rare cells have significant impact not only on monitoring cancer progress, but also on expanding the understanding of cancer metastasis. Rare cells also include fetal cells that are found in maternal blood. Various types of rare cells have been isolated and detected by several techniques based on fluorescence microscopy, microfluidic sorting, flow cytometry, genomic analysis, and immune-magnetic assays.

Conventional and advanced microscopy techniques are important diagnostic tools associated with the detection of a variety of targets such as viruses, bacteria, and mammalian cells. However, the costs of these techniques and their relative complexity challenge reliable and feasible implementation in rural areas and inner cities.

SUMMARY

Despite recent advances in detection techniques for cells (e.g., rare cells such as CTCs and fetal cells), viruses, and nucleic acids, a low-cost, portable, rapid, and robust detection platform for point-of-care (POC) diagnostics in resource-limited settings would provide significant advantages. The systems disclosed herein use imaging techniques, e.g., lens-less diffraction-based detection techniques such as, for example, holography, to identify labeled sample constituents such as cells, viruses, and nucleic acids in a variety of samples such as blood, to generate diffraction data.

By using a graphical processing unit to analyze (e.g., reconstruct) diffraction data, the analysis can be performed significantly more rapidly, permitting real-time or near real-time analysis and display of test results, such as images. Constituents of interest are labeled using methods that target specific binding sites (e.g., receptors or surface markers on a target in a sample, such as on a cell's outer membranes or specific base pair sequences in a nucleic acid). Such labeling changes the diffraction pattern produced by samples when exposed to illumination light. The change(s) in the diffraction pattern are then used to differentiate the target of interest from background.

For example, microbeads bound or conjugated to one or more binding moieties, such as antibodies, aptamers, antibody fragments, oligonucleotides, and oligopeptides, are used to target specific binding sites on the target sample constituents (e.g., tumor-specific antigens on CTCs or fetal-specific antigens on fetal blood cells), so that only constituents with the specific binding sites become bound to the microbeads. The target-bead conjugates generate diffraction patterns where the patterns from targets and beads are superimposed. Digital signal processing then de-convolves patterns corresponding to individual beads and target entities.

Rapid analysis of diffraction-based images, and identification and display of labeled sample constituents in the images, permits rapid, e.g., flow-based or static analysis of the samples. Such flow-based analysis is important, for example, when analyzing samples for the presence of rare cells (such as tumor, fetal, or infected cells) in relatively large volume samples. Because rare cells and other targets may be present in relatively low concentrations, larger sample volumes are typically analyzed, e.g., milliliters of samples, e.g., blood samples. Nonetheless, rapid processing of these larger sample volumes can still be achieved if the sample is flowed through the analysis systems described herein. Static imaging of sample volumes is also possible.

In general, in a first aspect, the disclosure features miniaturized diagnostic systems that include a radiation source, an aperture positioned to spatially filter radiation generated by the radiation source to generate at least partially coherent, spatially filtered radiation, a sample holder positioned so that a sample in or on the sample holder is exposed to the spatially filtered radiation wherein one or more of the constituents, e.g., cells (e.g., mammalian or bacterial cells), viruses, and nucleic acids, in the sample may be labeled, a detector configured to obtain one or more diffraction patterns of the sample in or on the sample holder, where each of the diffraction patterns includes information corresponding to optical properties of the spatially filtered radiation by the sample, and an electronic processor configured to, for each of the one or more diffraction patterns: (a) analyze the diffraction pattern to generate a reconstructed image of the sample; (b) analyze the reconstructed image of the sample to obtain optical information (phase and transmittance) corresponding to the diffraction of the spatially filtered radiation by the sample; (c) analyze the combined optical information and the diffraction pattern to obtain an improved reconstructed image of the sample; and (d) analyze the improved reconstructed image to identify labeled constituents, e.g., cells, in the sample.

Embodiments of the systems can include any one or more of the following features in any combination.

The detector can include at least one of a charge-coupled device (CCD) and a complementary metal-oxide semiconductor (CMOS) device. The detector can include a camera of a mobile telephone or tablet. The electronic processor can be a graphical processing unit of the mobile telephone or tablet. Alternatively, the electronic processor can be a remote graphical processing unit, and the system can include a wireless transmitter configured to transmit each of the diffraction patterns to the remote graphical processing unit. The electronic processor can be a graphical processing unit, e.g., a dedicated multi-core graphical processing unit.

The sample holder can include a fluid chamber, an inlet port connected to the fluid chamber, and an outlet port connected to the fluid chamber. The system can include a display unit, where the electronic processor is configured to display the identified labeled cells on the display unit. The display unit can be a screen of a mobile telephone or tablet.

The electronic processor can be configured to display the identified labeled cells in a first color, and to display unlabeled cells in the sample in a second color different from the first color.

The one or more diffraction patterns can include multiple diffraction patterns, and the electronic processor can be configured to identify one or more labeled constituents, e.g., cells (e.g., mammalian or bacterial cells), viruses, and nucleic acids, common to each of the improved reconstructed images generated from the multiple diffraction patterns. The labeled cells can include beads bound to the constituents, e.g., cells, and the electronic processor can be configured to determine, for each labeled constituent, a number of beads bound to the constituent. The electronic processor can be configured to display a histogram of the number of beads bound to the labeled constituents, e.g., cells.

Each of the reconstructed images can correspond to a portion of the sample flowing through the sample holder. The aperture can be separated from the radiation source by a distance of 1 mm or less. The sample holder can include a stage configured to support a glass slide.

The electronic processor can be configured to complete steps (a)-(d) in 0.1 second or less.

Embodiments of the systems can also include any of the other features disclosed herein, including features disclosed in connection with different embodiments, in any combination as appropriate.

In another aspect, the disclosure features methods for imaging a labeled sample that includes obtaining one or more diffraction patterns of the sample by illuminating the sample with spatially filtered, partially coherent radiation, and for each one of the one or more diffraction patterns: (a) analyzing the diffraction pattern to generate a reconstructed image of the sample; (b) analyzing the reconstructed image of the sample to obtain optical information corresponding to diffraction of the spatially filtered radiation by the sample; (c) analyzing the combined phase information and the diffraction pattern to obtain an improved reconstructed image of the sample; (d) analyzing the improved reconstructed image to identify labeled constituents, e.g., cells, in the sample; and (e) displaying the labeled constituents on a display unit.

Embodiments of the methods can include any one or more of the following features in any combination.

The methods can include performing steps (a)-(d) in 0.1 s or less. The one or more diffraction patterns can be obtained using a camera of a telephone or tablet. The method can include analyzing the one or more diffraction patterns using an electronic graphical processing unit. The methods can include using the telephone or tablet to wirelessly transmit the one or more diffraction patterns to a remote electronic graphical processing unit, and analyzing the one or more diffraction patterns using the remote electronic graphical processing unit.

The methods can include directing the sample to flow through a sample holder as the one or more diffraction patterns are obtained so that each reconstructed image corresponds to a portion of the sample flowing through the sample holder. The methods can include displaying the labeled constituents, e.g., cells, in a first color on the display unit, and displaying unlabeled constituents, e.g., cells, in the sample in a second color different from the first color on the display unit.

The one or more diffraction patterns can include multiple diffraction patterns, and the method can include identifying one or more labeled cells common to each of the reconstructed images generated from the multiple diffraction patterns.

The methods can include determining a number of labeled constituents, e.g., cells (e.g., mammalian or bacterial cells), viruses, and nucleic acids, per unit volume or per unit weight of the sample. The methods can include determining a number of labeled constituents, e.g., cells, in the sample based on the reconstructed image. The labeled cells can include beads bound to the cells, and the methods can include, for each labeled cell, determining a number of beads bound to the cell. The methods can include displaying a histogram of a number of beads bound to the labeled constituents, e.g., cells. The methods can include generating multiple improved reconstructed images from the one or more diffraction patterns, and displaying the labeled cells in each of the multiple improved reconstructed images on the display unit as a time-sequence of images.

The sample can include blood, and the labeled cells can be circulating tumor cells. The sample can include maternal blood, and the labeled cells can be fetal cells.

The methods can include obtaining the one or more diffraction patterns of the sample using a lens-free detector.

Analyzing the reconstructed image of the sample to obtain phase and transmittance information can include identifying a region of support in the reconstructed image for each of one or more cells in the reconstructed image. Determining the number of labeled cells in the sample can include, for each candidate cell in the improved reconstructed image, determining whether the candidate cell is an actual cell based on phase information corresponding to diffraction of the spatially filtered radiation by the candidate cell.

The methods can include identifying beads conjugated to the labeled cells based on phase information and intensity information corresponding to diffraction of the spatially filtered radiation by the sample. The methods can include identifying an object in the reconstructed image as a bead if a magnitude of phase information associated with the object is less than a selected threshold value and a magnitude of intensity information associated with the object is larger than a selected threshold value.

Embodiments of the methods can also include any of the other features or steps disclosed herein, including features or steps disclosed in connection with different embodiments, in any combination as appropriate.

In a further aspect, the disclosure features imaging apparatus that include a radiation source, an aperture positioned to spatially filter radiation generated by the radiation source to generate at least partially coherent, spatially filtered radiation, a sample holder positioned so that a sample in or on the sample holder is exposed to the spatially filtered radiation, and an attachment mechanism configured to connect the apparatus to a mobile telephone or tablet so that when the apparatus and the mobile telephone or tablet are connected, an image sensor of the mobile telephone is positioned to obtain one or more diffraction patterns of the sample in or on the sample holder, where each of the diffraction patterns includes information corresponding to the spatially filtered radiation by the sample.

Embodiments of the apparatus can include any one or more of the features disclosed herein, including features disclosed in connection with different embodiments, in any combination as appropriate.

In another aspect, the disclosure features diagnostic systems for measuring target constituents, e.g., cells (e.g., mammalian or bacterial cells), viruses, and nucleic acids, bound to labeling particles in a sample, the systems including a radiation source configured to generate illumination radiation, a sample holder configured to support the sample so that the sample is exposed to the illumination radiation, a detector configured to obtain one or more diffraction patterns of the sample, where each of the diffraction patterns includes information corresponding to optical properties of sample constituents, and an electronic processor configured to, for each of the one or more diffraction patterns: (a) analyze the diffraction pattern to obtain amplitude information and phase information corresponding to the sample constituents; (b) identify one or more particle-bound target sample constituents based on at least one of the amplitude information and the phase information; and (c) determine an amount of at least one of the particle-bound target sample constituents in the sample based on at least one of the amplitude information and the phase information.

Embodiments of the systems can include any one or more of the following features.

The systems can include an aperture configured to spatially filter the illumination radiation to generate partially coherent illumination radiation that is incident on the sample. The electronic processor can be configured to analyze the diffraction pattern by: (d) generating a reconstructed image of the sample; (e) analyzing the reconstructed image of the sample to obtain phase information corresponding to the diffraction of the illumination radiation by the sample; (f) analyzing the combined phase information and the diffraction pattern to obtain an improved reconstructed image of the sample; and (g) analyzing the improved reconstructed image to identify the one or more target sample constituents in the sample.

The detector can include at least one of a charge-coupled device (CCD) and a complementary metal-oxide semiconductor (CMOS) device. The detector can include a camera of a mobile telephone or tablet. The electronic processor can be a graphical processing unit of the mobile telephone or tablet.

The sample holder can include a fluid chamber, an inlet port connected to the fluid chamber, and an outlet port connected to the fluid chamber. The systems can include a display unit, where the electronic processor is configured to display the at least one of the target sample constituents on the display unit. The display unit can be a screen of a mobile telephone or tablet. The electronic processor can be configured to display the one or more target sample constituents in a first color, and to display other sample constituents in a second color different from the first color.

The one or more diffraction patterns can include multiple diffraction patterns, and the electronic processor can be configured to identify one or more target sample constituents common to each of the improved reconstructed images generated from the multiple diffraction patterns.

The one or more target sample constituents can include cells. The one or more target sample constituents can include beads bound to the cells, and the electronic processor can be configured to determine, for each cell, a number of beads bound to the cell. The one or more target sample constituents can include viruses. The one or more target sample constituents can include nucleic acids. The one or more target sample constituents can include bacteria. The electronic processor can be configured to display a histogram of the number of beads bound to each of the cells.

Each of the reconstructed images can correspond to a portion of the sample flowing through the sample holder. The aperture can be separated from the radiation source by a distance of 1 mm or less. The sample holder can include a stage configured to support a substrate bearing the sample. The electronic processor can be configured to complete steps (d)-(g) in 0.1 second or less.

Embodiments of the systems can also include any of the other features disclosed herein, including features disclosed in connection with different embodiments, in any combination as appropriate.

In a further aspect, the disclosure features methods for analyzing a sample, the methods including obtaining one or more diffraction patterns of the sample by illuminating the sample with spatially filtered, partially coherent radiation, and for each one of the one or more diffraction patterns: (a) analyzing the diffraction pattern to obtain amplitude information and phase information corresponding to diffraction of the illumination radiation by the sample; (b) identifying one or more target sample constituents, e.g., cells (e.g., mammalian or bacterial cells), viruses, and nucleic acids, based on at least one of the amplitude information and the phase information; and (c) determining an amount of at least one of the target sample constituents in the sample based on at least one of the amplitude information and the phase information.

Embodiments of the methods can include any one or more of the following features.

Analyzing the diffraction pattern can include: (d) generating a reconstructed image of the sample; (e) analyzing the reconstructed image of the sample to obtain phase information corresponding to the diffraction of the illumination radiation by the sample; (f) analyzing the combined phase information and the diffraction pattern to obtain an improved reconstructed image of the sample; and (g) analyzing the improved reconstructed image to identify the one or more target sample constituents, e.g., cells, in the sample. The methods can include performing steps (d)-(g) in 0.1 second or less.

The methods can include obtaining the one or more diffraction patterns using a camera of a mobile telephone or tablet. The methods can include analyzing the diffraction patterns using an electronic graphical processing unit. The methods can include using the mobile telephone or tablet to wirelessly transmit the one or more diffraction patterns to a remote electronic graphical processing unit, and analyzing the one or more diffraction patterns using the remote electronic graphical processing unit.

The methods can include directing the sample to flow through a sample holder as the one or more diffraction patterns are obtained so that each reconstructed image corresponds to a portion of the sample flowing through the sample holder. The methods can include displaying the one or more target sample constituents in a first color on the display unit, and displaying other sample constituents in a second color different from the first color on the display unit.

The one or more diffraction patterns can include multiple diffraction patterns, and the methods can include identifying one or more target sample constituents common to each of the reconstructed images generated from the multiple diffraction patterns. The methods can include determining a number of labeled target sample constituents per unit volume or per unit weight of the sample based on at least one of the amplitude information and the phase information. The methods can include determining a number of labeled target sample constituents in the sample based on the reconstructed image.

The one or more target sample constituents can include cells. The one or more target sample constituents can include beads bound to the cells, and the methods can include, for each cell that includes beads, determining a number of beads bound to the cell. The methods can include displaying a histogram of the number of beads bound to each of the cells. The one or more target sample constituents can include viruses. The one or more target sample constituents can include nucleic acids. The one or more target sample constituents can include bacteria. The sample can include blood, and the target sample constituents can include circulating tumor cells. The sample can include maternal blood, and the target sample constituents can include fetal cells.

The methods can include generating multiple improved reconstructed images from the one or more diffraction patterns, and displaying the one or more target sample constituents in each of the multiple improved reconstructed images on a display unit as a time-sequence of images. The methods can include obtaining the one or more diffraction patterns of the sample using a lens-free detector. Analyzing the reconstructed image of the sample to obtain phase information can include identifying a region of support in the reconstructed image for each of one or more target sample constituents in the reconstructed image.

The labeled target sample constituents can include labeled cells, and determining the number of labeled cells can include, for each candidate cell in the improved reconstructed image, determining whether the candidate cell is an actual cell based on phase information corresponding to diffraction of the spatially filtered radiation by the candidate cell. The target sample constituents can include cells, and the methods can include identifying beads conjugated to the cells based on at least one of the phase information and the intensity information corresponding to diffraction of the spatially filtered radiation by the sample. The methods can include identifying an object in the reconstructed image as a bead if a magnitude of phase information associated with the object is less than a first selected threshold value and a magnitude of intensity information associated with the object is larger than a second selected threshold value.

The methods can include labeling the target sample constituents prior to illuminating the sample. Labeling the target sample constituents can include binding the target sample constituents to particles. Optical properties of the labeled target sample constituents can be different from optical properties of unlabeled sample constituents. The methods can include labeling different types of target sample constituents by binding the different types of target sample constituents to different types of particles. Each different type of labeled target sample constituents can have optical properties different from other types of labeled target sample constituents. Labeling the target sample constituents can include binding the target sample constituents to nanoparticles, e.g., gold nanoparticles. The methods can include depositing a coating on the labeled target sample constituents, e.g., a coating that includes silver.

Embodiments of the methods can also include any of the other steps and features disclosed herein, including steps and features disclosed in connection with different embodiments, in any combination as appropriate.

In another aspect, the disclosure features imaging apparatus that include a radiation source, an aperture positioned to spatially filter radiation generated by the radiation source to generate at least partially coherent, spatially filtered radiation, a sample holder positioned so that a sample in or on the sample holder is exposed to the spatially filtered radiation, and an attachment mechanism configured to connect the apparatus to a mobile telephone or tablet so that when the apparatus and the mobile telephone or tablet are connected, an image sensor of the mobile telephone or tablet is positioned to obtain one or more diffraction patterns of the sample in or on the sample holder, wherein each of the diffraction patterns comprises information corresponding to diffraction of the spatially filtered radiation by the sample.

Embodiments of the apparatus can include any one or more of the features disclosed herein, including features disclosed in connection with different embodiments, in any combination as appropriate.

Unless otherwise defined, all technical and scientific terms used herein have the same meaning as commonly understood by one of ordinary skill in the art to which this disclosure belongs. Although methods and materials similar or equivalent to those described herein can be used in the practice or testing of the subject matter herein, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments are set forth in the accompanying drawings and the description below. Other features and advantages will be apparent from the description, drawings, and claims.

DESCRIPTION OF DRAWINGS

FIG. 11B is a graph showing average bead count for each of the patient samples of FIG. 11A.

FIG. 11C is a graph showing the distribution of average bead counts for the patient samples of FIG. 11A.

FIG. 11D is a receiver operation characteristic curve for the high-risk vs. low-risk sample groups of FIG. 11A.

FIG. 11E is a schematic diagram showing a process for applying Ag coatings to microspheres that have captured nucleic acid targets.

FIG. 12A is a graph showing measured bead sizes as a function of nominal bead sizes.

FIG. 12B is a graph showing transmittance values for different bead types.

FIG. 12C is a graph showing lymphoma cell size measurements for Daudi cells.

Like reference symbols in the various drawings indicate like elements.

DETAILED DESCRIPTION

Introduction—Point-of-Care Molecular Diagnosis

Figure 1A:
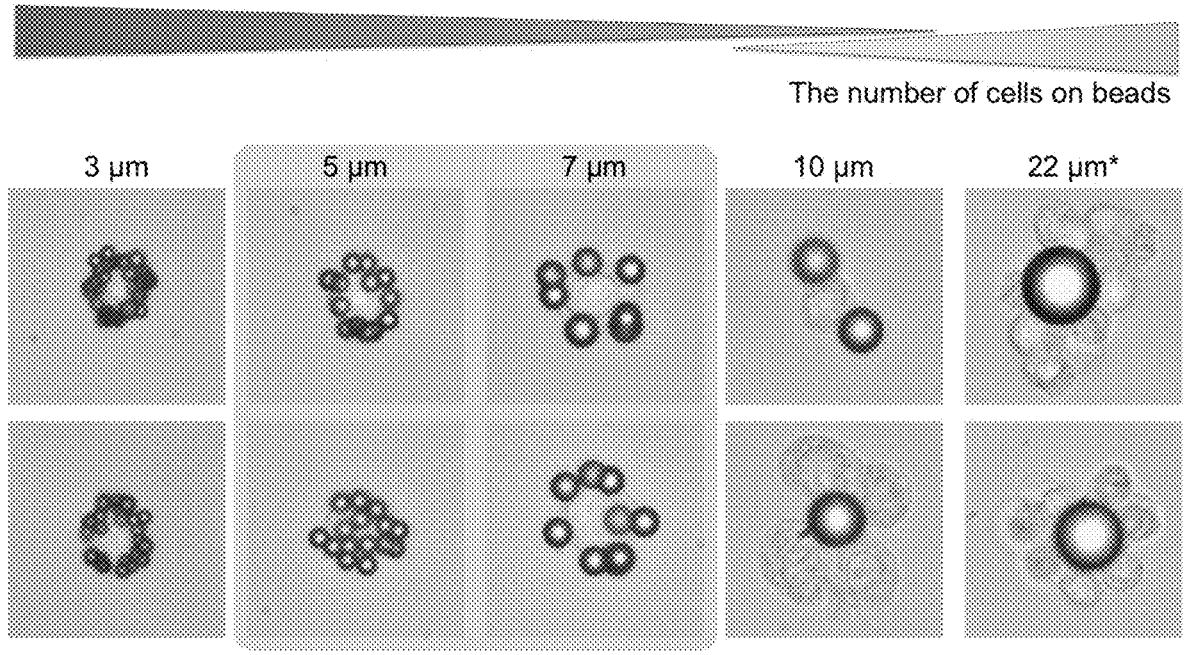
FIG. 1A is a sequence of images of differently-sized beads conjugated to cells.

Detecting and quantifying sample constituents such as cells, viruses, and nucleic acids in a sample (e.g., blood) using a simple, low-cost apparatus can be a challenging problem. For example, where relatively rare cells (e.g., cancer cells, bacteria) are the target for detection, the cells can often be dispersed among millions of other cells in the sample. As another example, where viruses (e.g., human papilloma virus (HPV)) and/or nucleic acids are the target for detection, the small size of these targets presents significant imaging challenges.

To achieve robust detection, molecular signatures of target cells, viruses, nucleic acids, and/or other detection targets must be identified with high specificity and sensitivity. Moreover, because the detection of these targets provides important diagnostic information for physicians, simple and low-cost methods for reliable identification are highly desirable. Unfortunately, existing technologies for such detection are typically complex and expensive.

The present disclosure features methods and systems for identifying sample constituents such as cells (e.g., rare cells), viruses, nucleic acids (e.g., DNA and/or RNA), bacteria, proteins, small molecules, and/or microvesicles in biological samples. Although cells, viruses, and nucleic acids are described as examples herein, it should be understood that the methods and systems disclosed herein can also be used for other sample constituents. Moreover, the methods and systems can be used to detect constituents in a wide variety of sample types (e.g., blood and/or other biological fluids, environmental samples such as water from streams, rivers, lakes, oceans, ponds, and pools, and foods and beverages) by employing similar labeling, imaging, and analysis techniques. The methods and systems disclosed herein are highly sensitive, and provide real-time or near real-time analysis of sample images to identify biological targets of interest. Further, the methods and systems are implemented using low-cost hardware enabling point-of-care applications in a wide variety of settings.

As a first step in the analysis of a sample, sample constituents are targeted by labeling agents that can generate a distinct optical signature based on diffraction patterns. Such agents include, but not limited to, microbeads or microparticles, or nanobeads or nanoparticles, conjugated to binding moieties that specifically bind to particular binding sites on the sample constituents. For example, antibody-conjugated microbeads (e.g., polystyrene microbeads) that include antibodies that bind specifically to tumor-specific antigens on the surface of a particular type of cancer cell can be used to label those cancer cells for analysis by the new methods and systems described herein. The sample—which can include both labeled and unlabeled constituents (e.g., cells, viruses, and/or nucleic acids)—is then introduced into the detection system that obtains one or more diffraction patterns of the sample. Various techniques can be used to obtain images in which the labeled sample constituents are distinguishable from the non-labeled constituents. As an example, holographic imaging can be used to obtain images that are suitable.

Analysis of the images (for example, by digital reconstruction of diffraction patterns) allows targeted sample constituents to be distinguished from non-targeted constituents in the sample based on the presence of micro- or nanoparticles bound to the targeted constituents. The specific labeling of targeted constituents permits thousands of micro- or nanoparticles or beads and constituents to be accurately counted at raw concentrations without any dilution or washing steps. In this manner, target sample constituents can not only be identified visually in a sample, but the constituent amounts can be accurately quantified.

The term "binding," as used herein, refers to the interaction between a corresponding pair of molecules or portions thereof that exhibit mutual affinity or binding capacity, typically due to specific or non-specific binding or interaction, including, but not limited to, biochemical, physiological, and/or chemical interactions. "Specific binding" refers to binding by molecules, such as polynucleotides, antibodies, and other ligands, that are able to bind to or recognize a binding partner (or a limited number of binding partners), such as a surface marker, e.g., an antigen, to a substantially higher degree than to other, similar biological entities. For purposes of this disclosure, specific binding means the targeting moiety has a specificity (as measured via a dissociation constant) of at least about 10 micromolar.

Labeling Sample Constituents

The first step in analyzing a sample involves labeling target sample constituents with molecular-specific micro- and/or nanoparticles. Such labeling enables 1) reliable differentiation between target constituents and non-target constituents, and 2) quantitative profiling of the target constituents by counting the labeling micro- and/or nanoparticles. Typically, labeling either enhances contrast in sample images and/or generates distinct diffraction patterns between target and non-target constituents, assisting subsequent image analysis. As an example, when specific cells in a blood sample are targeted, labeling allows target cells (e.g., cancer cells) to be differentiated from non-target cells (e.g., blood cells such as white blood cells (leukocytes) or other circulating cells such as epithelial cells). Multiple different target constituents can be labeled in the same sample, each with a different and distinct label.

In general, the labeling methods disclosed herein allow for analyzing multiple different target constituents by using micro- and/or nanoparticles that have distinctive optical properties, and can therefore be distinguished from one another in sample images. As will be discussed below with reference to specific examples, micro- and/or nanoparticles of different sizes can be readily distinguished from one another in, e.g., diffraction images, on the basis of their diffraction intensity, reconstructed transmittance, and/or reconstructed phase values.

Further, by using micro- and/or nanoparticles formed from different materials, the wavelength at which the particles absorb incident light can be controlled. As a result, the spectrum of light transmitted through such particles will vary according to the absorption spectrum of the particles. Further, specific particles can be interrogated by tuning the wavelength of illumination light to match the absorption spectrum of the target particles.

Even when the particles are formed from similar materials, the particles can be coated with different materials such that differently coated particles (and uncoated particles) can have different transmittance values. For example, as will be described in more detail below shell coatings of materials such as Ag can be used to impart different transmittance values to certain particles, thereby allowing such particles to be distinguished in sample images.

In general, some or all of these attributes can be combined to produce micro- and/or nanoparticles that target certain sample constituents. Further, because of the large number of combinations of size, spectral, and transmittance properties that can be engineered into the particles, cocktails of multiple different types of particles—targeting multiple different sample constituents—can be used for multiplex analysis of samples. Such methods are useful, for example, when analyzing a sample that may contain a variety of different constituents of interest, such as in multi-disease assays. Such methods can also be useful in multi-probe assays for particular conditions, e.g., when diagnosis of a specific condition is dependent upon identification of multiple different markers—such as multiple gene sequences—in a sample. Multiplex methods are also useful for more detailed diagnoses, such as for example when diagnosing a disease with multiple sub-types.

Multiplexed analysis with micro- and/or nanoparticles of different sizes and/or spectral properties (i.e., "colors") and/or transmittance values allows for multiple multiplexing "channels" to be analyzed at the same time. In addition to a selected size, color, and transmittance value, micro- and/or nanoparticles with combinations of one or more of these parameters can be fabricated. For example, in addition to producing particles that are absorb in the red, green, or blue regions of the electromagnetic spectrum, particles can also be fabricated that absorb in the red and green, or red and blue, or green and blue, regions. Thus, between three and six color combinations can be distinguished from one another, providing a minimum of 3-6 multiplex channels based on color attributes alone.

By combining size, absorption color, and transmittance value, even more multiplex channels for sample analysis can be created. In some embodiments, for example, the number of independent channels—corresponding to different sample constituents—that can be analyzed is 3 or more (e.g., 6 or more, 9 or more, 12 or more, 15 or more, 20 or more).

To interrogate micro- and/or nanoparticles that correspond to different colors, the systems disclosed herein include one or more wavelength-selective elements. In some embodiments, for example, the wavelength-selective elements filter transmitted radiation before it reaches the detector, to selectively remove contributions corresponding to micro- and/or nanoparticles bound to certain sample constituents. In certain embodiments, the wavelength-selective elements filter illumination radiation so that illumination radiation provided to the sample is selectively absorbed or excites only micro- and/or nanoparticles bound to constituents of interest. Wavelength-selective elements can include, for example, static filters and/or reconfigurable filters such as filter wheels and liquid crystal-based filters. In some embodiments, the light source used to illuminate the sample is configurable, and selectively produces illumination light at one or more desired wavelengths under the control of a system controller or electronic processor. As an example, the light source can include multiple LEDs that can be selectively activated to generate illumination light of varying wavelengths.

In some implementations, the labeling process involves two steps. First, binding moieties are bound to specific sites on target sample constituents. Second, the binding moieties are conjugated to micro- or nanoparticles to mark the presence of the specific sites on the target sample constituents. As an example, to target specific cells in a sample, antibodies can be bound to specific surface markers (e.g., antigens) on the target cells (e.g., tumor-specific antigens on target CTCs or fetal-specific antigens on target fetal cells in maternal blood). Then, the antibodies bound to the surface of the target cells are conjugated to microbeads (e.g., polystyrene or silica microbeads) to mark the presence of the specific antigens on the cells.

While the foregoing two-step conjugation method has been shown to work well for labeling sample constituents, in some embodiments direct immuno-conjugation labeling techniques can also be used, where the binding moieties are first conjugated to micro- and/or nanoparticles, and then the particles are bound to the target sample constituents via the binding moieties. In some embodiments, after labeling, the number of specific binding sites on the target sample constituents can be estimated by the number of micro- and/or nanoparticles attached to the constituents and/or the contrast conferred by the micro- and/or nanoparticles. The more micro- and/or nanoparticles that are bound to the constituents, the higher the number of specific binding sites on the sample constituents. For certain target constituents, the amount of contrast conferred by the micro- and/or nanoparticles can be used to estimate the concentration of the target constituents in the sample.

The micro- and/or nanoparticles (e.g., microbeads) can be made of various materials. In general, any polymeric or plastic materials can be used to create the microparticles, microbeads, or nanoparticles, including materials such as polystyrene and polyethylene, for example. In some embodiments, microparticles can be formed of biologically-compatible polymer materials such as polyacrylates, polymethacrylates, and/or polyamides.

In certain embodiments, metallic, metal-oxide, semiconductor, and/or semiconductor-oxide micro- and/or nanoparticles formed from one or more of Au, Ag, Pt, Al, Cu, Ni, Fe, Cd, Se, Ge, Pd, Sn, iron oxide, $TiO_2$, $Al_2O_3$, and $SiO_2$ can be made in many sizes and used. For example, monocrystalline iron oxide nanoparticles (MIONs) and crosslinked iron oxide (CLIO) particles can be used. As another example, quantum dots (similar to nanoparticles) of CdSe and other semiconductors can be used. In some embodiments, combinations of different metallic and semiconductor materials can be used. For example, micro- and/or nanoparticles can be formed from $TiO_2$ on Au, $Al_2O_3$ on Au, $SiO_2$ on Au, Ag on Au, and Au on $TiO_2$.

Metal- and semiconductor-based particles can be micron or nanometer sized; some are known to provide enhanced contrast in imaging (e.g., nanoparticles that emit at specific wavelengths, which produces the enhanced contrast, even though they may be too small to be counted individually). Provided that such particles can be conjugated to binding moieties, they can be used in the methods disclosed herein.

In certain embodiments, materials such as silica, glass, calcium carbonate, mica, zeolites, and/or ceramic materials such as magnetite can be used to form micro- and/or nanoparticles.

In some embodiments, various paramagnetic and superparamagnetic particles micro- and/or nanoparticles can also be used as long as they can be conjugated to binding moieties. Magnetic particles may be useful in certain embodiments, as long as they do not clump together. Beads with magnetic particles (e.g., magnetic beads) can be used to facilitate magnetic manipulation of target cells.

Still further, micro- and/or nanoparticles for sample constituent labeling can be formed from other materials as well. FIG. 1B is a graph showing various materials from which suitable micro- and/or nanoparticles can be formed, and the corresponding fluorescence wavelength shift (relative to an excitation wavelength) for each material.

For detection of target cells in a sample, if the particles are made of plastic or polymers, then they typically have a diameter no larger than the diameter of the cell, so that multiple particles can bind to each cell rather than having multiple cells bound to each microparticle (which could confound counting of the cells). For example, given cells with a diameter of about 10 µm, the microparticles should have a diameter of about 1 to 9 µm, e.g., 2 to 8 µm, 3 to 7 µm, or 5 to 7 µm. In one example, cancer cells (which have a diameter of about 10 µm) were tested with different sizes of microbeads ranging from 3 to 22 µm in diameter. Microbeads with diameters between 5 and 7 µm beads were found to provide the best visualization of the expression levels of the surface antigens on the cancer cells by the number of beads captured on the cancer cell. More generally, however, particles with diameter ranges from nanometers to micrometers can be used to label sample constituents.

Figure 1B:
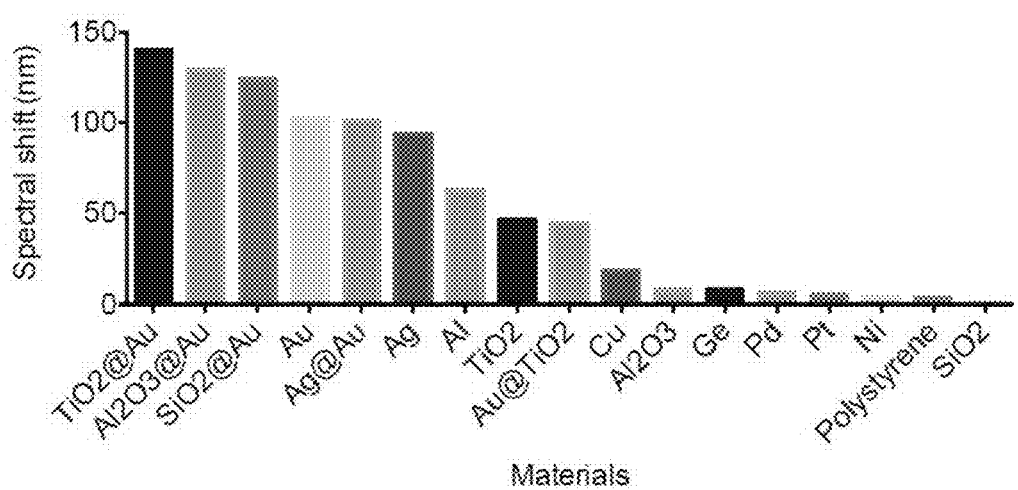
FIG. 1B is a graph showing spectral shifts for some materials that can be used to form micro- and/or nanoparticles for labeling samples.

FIG. 1A shows a series of images of different sizes of microbeads conjugated to cancer cells. As is evident, the maximum number of beads attached to the cells decreases as the size of bead increases up to 10 µm. When the size of bead was larger than 10 µm, the cells tend to be attached to the bead (i.e., multiple cells are attached to a single bead). Particles made of metals and ceramics can be on the nanoscale, e.g., 10 to 1000 nm, e.g., 200-800 nm, 250-750 nm, or 300-500 nm.

The binding (or targeting) moiety can be or include a nucleic acid, nucleic acid ligands (e.g., aptamers), polypeptide, protein ligand, small molecule, growth factor, hormone, cytokine, interleukin, antibody, antibody fragment, integrin, fibronectin receptor, carbohydrate, p-glycoprotein receptor, peptide, peptidomimetic, hydrocarbon, small modular immunopharmaceutical, or a binding sequence (e.g., a cell binding sequence). For example, the protein ligands can be or include an affibody, nanobody, adnectin, domain antibody, or an avimer, or any combination thereof. As another example, the targeting moiety can be a peptide with fewer than 8 amino acids, or the targeting moiety can bind to a basement membrane, or to the Prostate Specific Membrane Antigen (PSMA). The binding moieties can be bound or conjugated to the surface of the micro- and/or nanoparticles directly or via a functional group.

Binding moieties in the form of nucleic acid ligands, such as aptamers, are small oligonucleotides that specifically bind to certain target molecules and are potential candidates to target proteins over-expressed in cancer cells, such as prostate cancer cells. A nucleic acid ligand is a nucleic acid that can be used to bind to a specific molecule. For example, pegaptanib is a pegylated anti-VEGF aptamer, a single stranded nucleic acid that binds with high specificity to a particular target. Specific aptamers include, for example, Aptamer O-7 which binds to osteoblasts; A10 RNA aptamer, which binds to prostate cancer cells; aptamer TTA1, which binds to breast cancer cells; and the extended A9 RNA aptamer (Javier et al., Bioconjug Chem. 2008 Jun. 18; 19(6):1309-1312). See also, Wilson et al., U.S. Published Patent Application No. 20090105172. See also, PCT WO 2010/042555, which is incorporated herein by reference in its entirety for its description of various binding moieties that can be used for targeting particular types of sample constituents as well as for materials that can be used to form micro- and/or nanoparticles.

In some embodiments, metal-coated, e.g., Ag-coated micro- and/or nanoparticles (e.g., beads) are used for detection and analysis of sample constituents. For example, Ag-coated particles strongly absorb incident light at certain wavelengths in the visible region of the electromagnetic spectrum (e.g., at about 470 nm), and therefore, sample constituents labeled with such nanoparticles contrast strongly with unlabeled sample constituents in images and are readily identified.

Figure 1C:
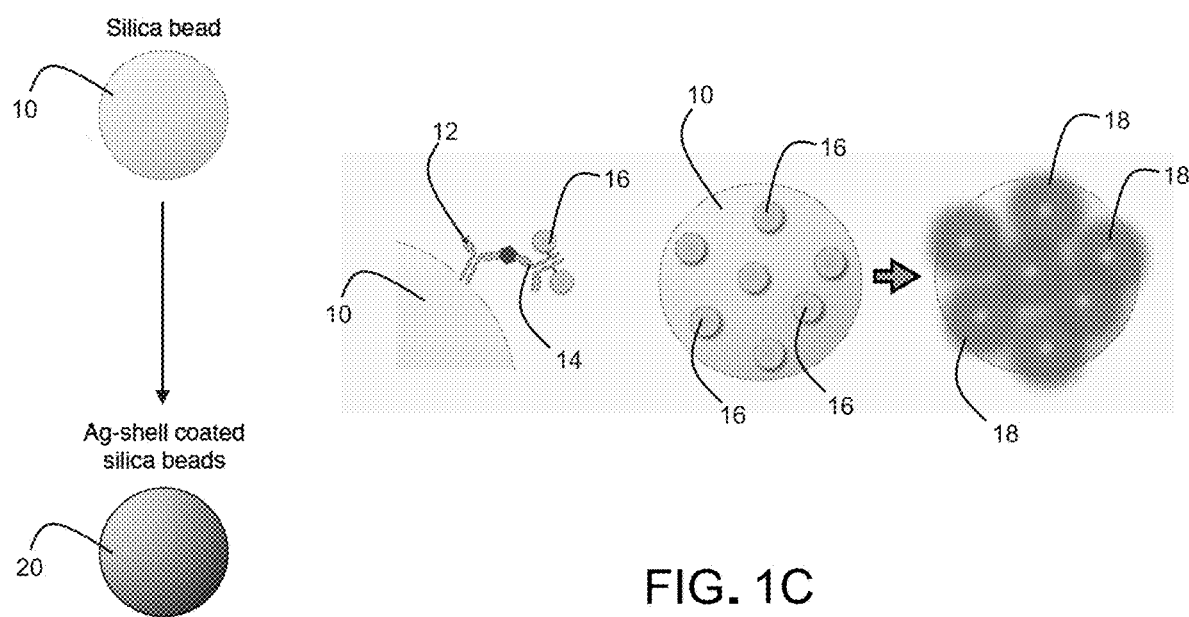
FIG. 1C is a schematic diagram showing a process for forming Ag shells on silica beads.

FIG. 1C shows a schematic diagram of a method for forming suitable metal-coated, e.g., Ag-coated particles. Silica microspheres 10 are functionalized with affinity ligands that can include, for example, peptides, antibodies, and/or oligonucleotides (examples of which are described above) with complementary sequences that bind to sample constituents 12 that feature binding sites, as described above. Such constituents can include, for example, proteins and/or nucleic acids. Silica microspheres 10 can, in general, be of any desired size. For example, silica microspheres with diameters of between 3 microns and 10 microns are suitable.

After sample constituents 12 are bound to microspheres 10, sample constituents 12 are labeled with Au nanoparticles 16 via binding partners 14. In general, Au nanoparticles of a variety of different sizes can be used. In some embodiments, for example, Au nanoparticles 16 with diameters of between 10 nm and 30 nm are used. Binding partners 14, in general, include moieties that bind to both sample constituents 12 and Au nanoparticles 16. A wide variety of different binding partners 14 can be used, including for example peptides, antibodies, and/or oligonucleotides (examples of which are described above) similar to sample constituents 12.

The foregoing method yields a sandwich-assay in which two binding partners (e.g., functionalized silica microspheres 10 and binding partners 14) are used to capture and label sample constituents 12 with Au nanoparticles 16. Following labeling with Au nanoparticles 16, shells of Ag are grown, using the Au nanoparticles 16 conjugated on silica microspheres 10 as seed sites. At first, Ag shells grow on Au nanoparticles 16, yielding Ag-coated Au nanoparticles 18. As Ag shell growth proceeds, the Ag shells extend to cover much or even all of the microspheres within about 5 minutes. The Ag-coated microspheres 20 are generally optically opaque.

Accordingly, it is the presence of target sample constituents 12 that leads to the growth of Ag shells on silica microspheres 10, which changes the transmittance of the microspheres. Such changes can be detected by analyzing intensity profiles in sample images (e.g., diffraction patterns) or in analyzed images (e.g., reconstructed images).

Figure 1D:
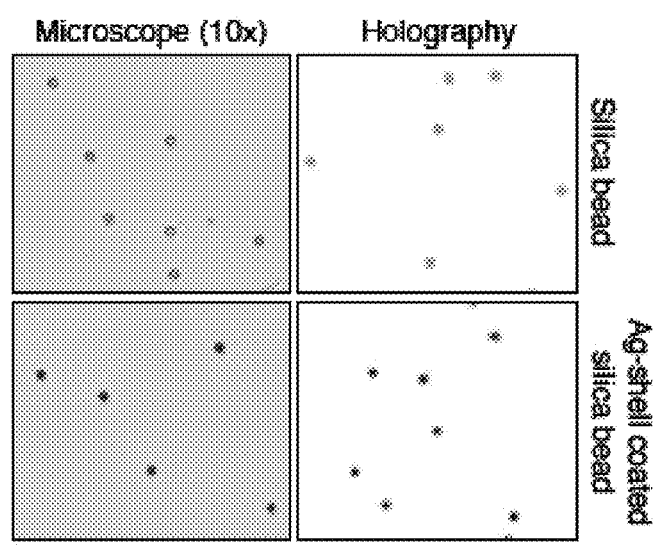
FIG. 1D is a sequence of images showing optical microscope and diffraction images of uncoated silica beads and silica beads coated with Ag shells.

FIG. 1D shows microscope and reconstructed diffraction patterns of silica microspheres before and after Ag shell growth. As is evident from the images in the figure, the contrast imparted to the microspheres is greater in both microscope and reconstructed diffraction patterns following Ag shell growth, facilitating detection of the microspheres.

Figure 1E:
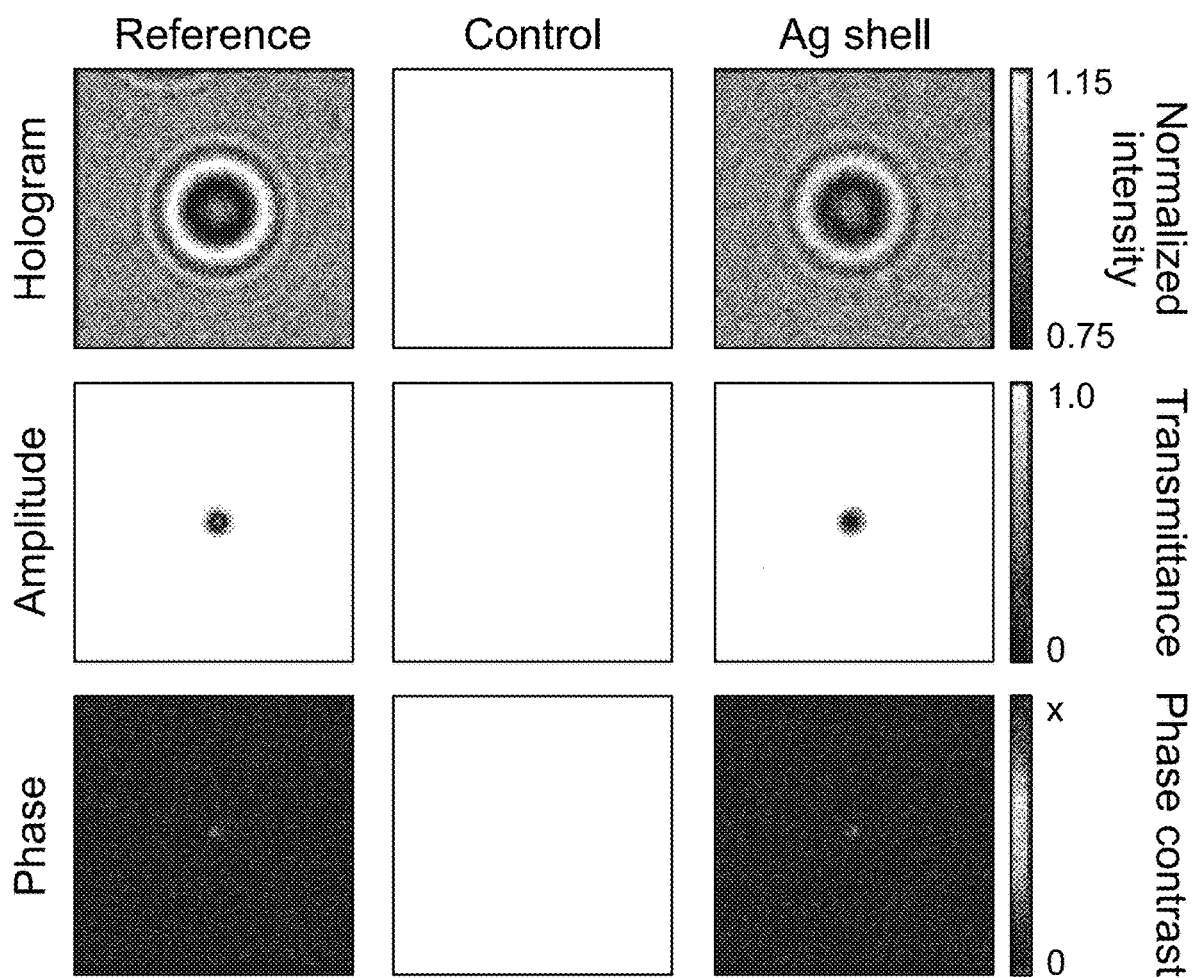
FIG. 1E is a sequence of diffraction, reconstructed transmittance, and reconstructed phase images for a reference bead, a control bead, and a bead with a Ag coating.

To investigate detection of Ag-coated microspheres, a simple biotin-avidin model was tested using avidin-conjugated silica microspheres (diameter 7 µm) and biotinylated Au nanoparticles (diameter 20 nm). The same size of Au nanoparticles coated with polyethylene glycol (PEG) were used as a negative control. FIG. 1E shows diffraction patterns, reconstructed amplitudes, and reconstructed phases, for a reference microsphere, a control microsphere, and an Ag-coated microsphere. The reference microsphere was an uncoated silica microsphere, and the control microsphere had PEG-coated nanoparticles bound to its surface.

Figure 1F:
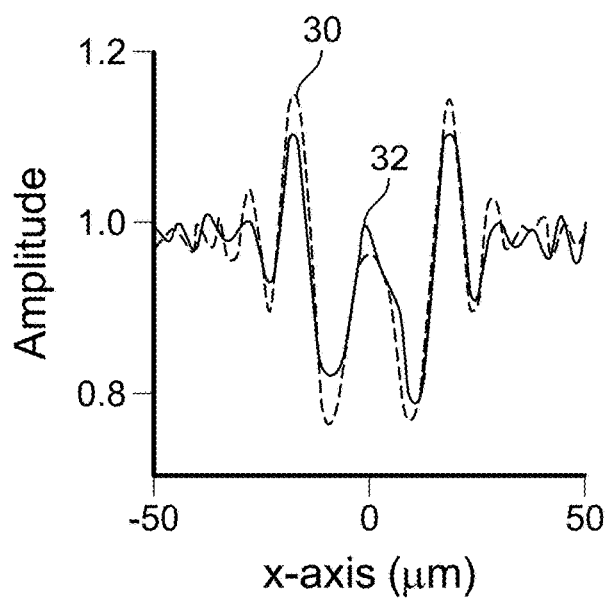
FIG. 1F is a profile graph showing diffraction image intensity as a function of position for the reference and coated beads of FIG. 1E.
Figure 1G:
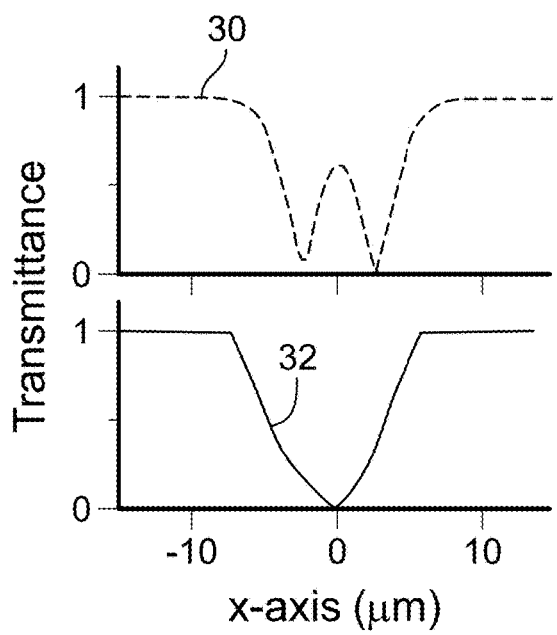
FIG. 1G is a profile graph showing reconstructed transmittance as a function of position for the reference and coated beads of FIG. 1E.
Figure 1H:
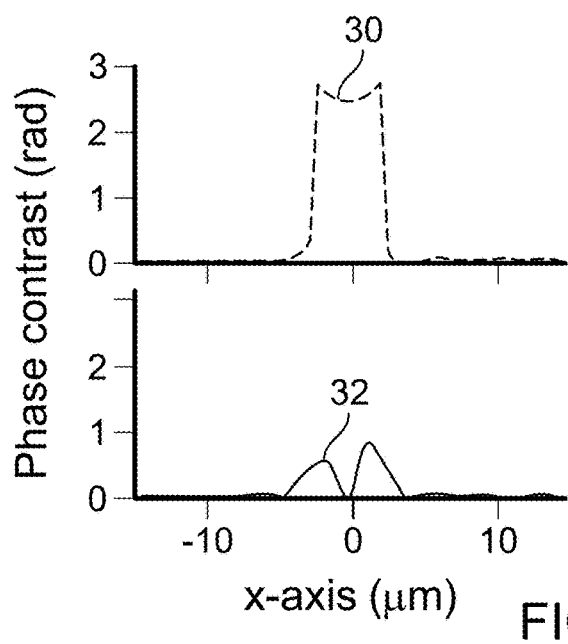
FIG. 1H is a profile graph showing reconstructed phase as a function of position for the reference and coated beads of FIG. 1E.

FIG. 1F is a plot showing a comparison between cross-sectional intensity profiles of the reference microspheres 30 and Ag-coated 32 microspheres. FIGS. 1G and 1H are plots showing a comparison between cross-sectional amplitude (i.e., transmittance) and phase profiles of the reference 30 and Ag-coated 32 microspheres. While differences between the reference and Ag-coated microspheres can be detected based on intensity, the differences between the microspheres is more pronounced in the amplitude and phase profiles. The silica microspheres, with a refractive index of about 1.4, are optically transparent in water, and therefore can readily be detected in phase contrast images. When coated with Ag shells, however, light transmission (e.g., amplitude) decreases due to the shells, and phase contrast also therefore decreases. Because Ag shells are grown on Au nanoparticles only when target sample constituents are conjugated to the nanoparticles (and to the microspheres), changes in transmittance and phase contrast can be used as indicators of the presence of the target sample constituents. In contrast, the control microsphere did not show significant detectable changes in transmittance or phase contrast, relative to a bare microsphere.

It should also be noted that while changes in transmittance and/or phase contrast result from the binding of Au nanoparticles to the target sample constituents, the growth of the Ag shells further amplifies the modulation of the transmittance and/or phase contrast, making the target sample constituents easier to detect, and increasing the dynamic range over which changes in transmittance and/or phase contrast can be detected.

Figure 1I:
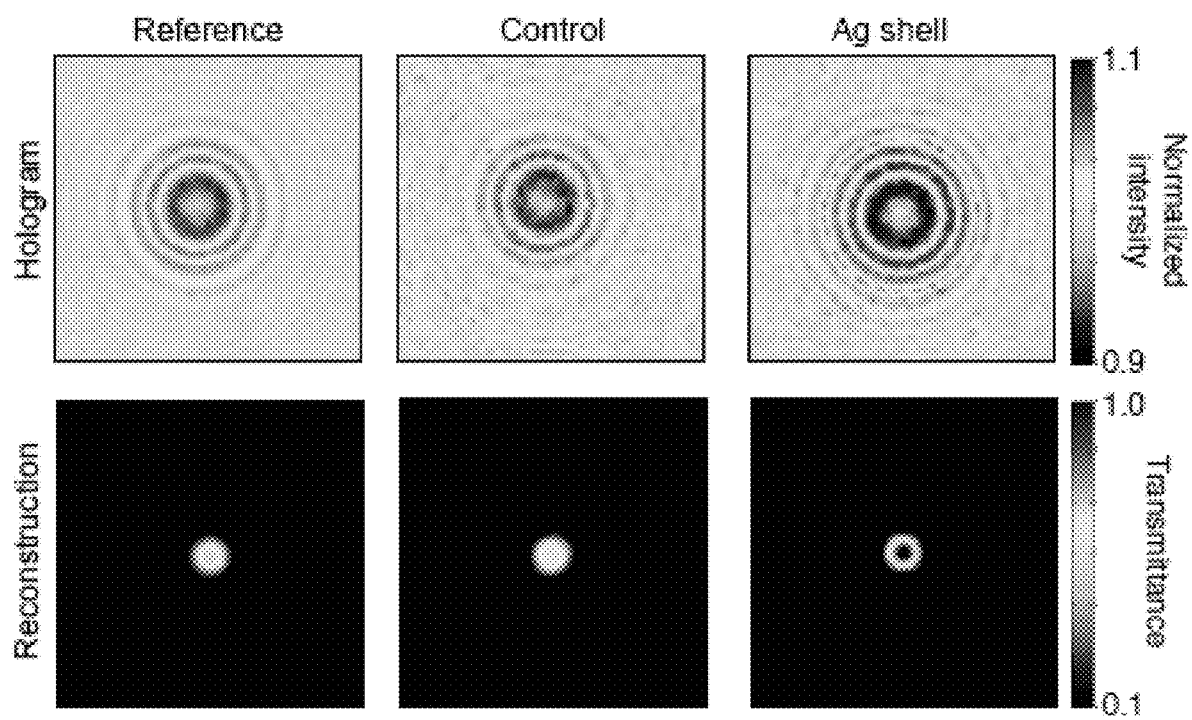
FIG. 1I is a sequence of diffraction and reconstructed transmittance images of a reference bead, a control bead, and a bead with an Ag coated.
Figures 1J, 1K:
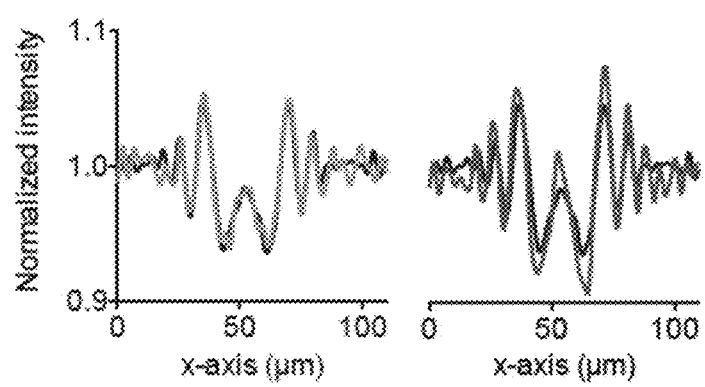
FIG. 1J is a profile graph showing diffraction image intensity as a function of position for the control and reference beads of FIG. 1I.
FIG. 1K is a profile graph showing diffraction image intensity as a function of position for the reference and Ag coated beads of FIG. 1I.

FIG. 1I shows an additional set of diffraction patterns and reconstructed amplitude images for reference, control and Ag-coated microspheres as described above. FIGS. 1J and 1K are plots comparing intensity profiles for the control and reference microspheres (FIG. 1J) and the reference and Ag-coated microspheres (FIG. 1K). As shown in FIG. 1J, the intensity profiles for the control and reference microspheres are very similar. Moderate differences in modulation are detectable for the reference and Ag-coated microspheres, as shown in FIG. 1K.

Figure 1L:
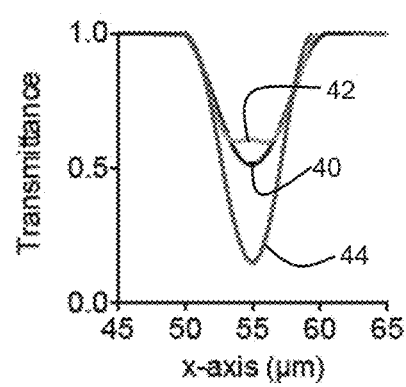
FIG. 1L is a profile graph showing reconstructed transmittance as a function of position for the reference, control, and Ag coated beads of FIG. 1I.

FIG. 1L shows reconstructed transmittance profiles for the reference 40, control 42, and Ag-coated 44 microspheres. Significant differences are apparent among the three different microspheres, meaning that the reconstructed transmittance information can readily be used to distinguish among these different types of microspheres.

Capture and target probes can be conjugated to microspheres and nanoparticles using a variety of covalent reactions, including for example NETS-ester conjugation, thiol-amine conjugation, and TCO-Tz conjugation. Methods for performing such conjugations are described, for example, in Chung et al., *Nature Nanotechnology* 8(5): 369-375 (2013), in Liong et al., *Nature Communications* 4:1752 (2013), and in Haun et al., *Nature Nanotechnology* 5(9): 280-293 (2010), the entire contents of each of which are incorporated by reference herein.

Figure 1M:
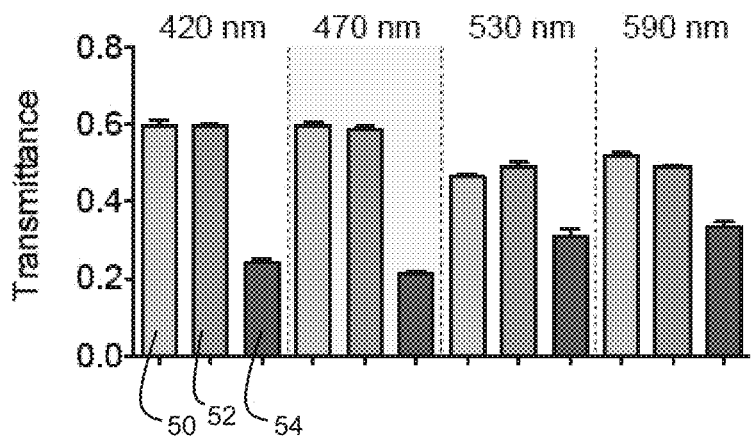
FIG. 1M is a graph showing reconstructed transmittance values as a function of illumination wavelength for the reference, control, and Ag coated beads of FIG. 1I.

To investigate the effect of the Ag shells on the light transmission properties of the silica microspheres, Ag-coated microspheres were tested by exposing the microspheres to four different wavelengths of incident light from 420 nm to 590 nm. More than 50 microspheres were analyzed at each wavelength, including reference, control, and Ag-coated microspheres as described above. FIG. 1M is a plot of transmittance for the reference 50, control 52, and Ag-coated 54 microspheres at each incident light wavelength. Ag-coated microspheres showed the largest decrease in transmittance (i.e., strongest light absorption by Ag) at 470 nm. Measured variations were reproducible to within 3%.

Figure 1N:
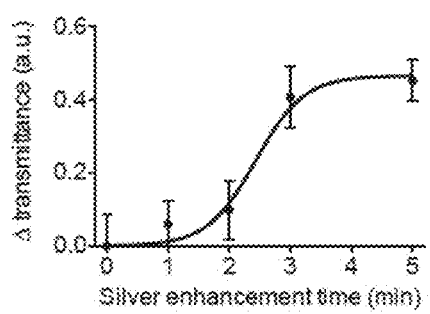
FIG. 1N is a graph showing change in transmittance value as a function of time for the Ag coated bead of FIG. 1I.

FIG. 1N is a plot showing change in transmittance for the Ag-coated microspheres as a function of time. The transmittance change saturated after about 5 minutes, suggesting that the formation of the Ag shells proceeded by a fast catalyzed reaction.

Figure 1O:
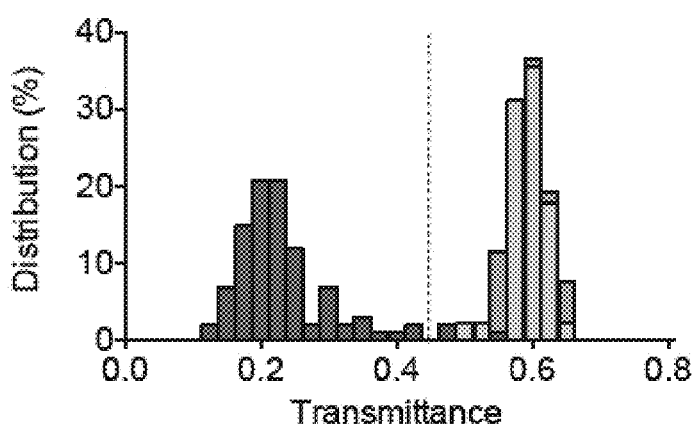
FIG. 1O is a histogram showing distributions of reconstructed transmittance values for the reference, control, and Ag coated beads of FIG. 1I.

FIG. 1O is a histogram showing distributions of transmittance values of Ag-coated, control, and reference microspheres. Nearly all of the Ag-coated microspheres are positioned to the left of the dashed line in the figure, while nearly all of the reference and control microspheres are positioned to the right of the dashed line. The threshold transmittance value of 0.45 corresponding to the dashed line and representing a marked separation point between the Ag-coated and non-Ag-coated microspheres, proved to be a reliable diagnostic for distinguishing between these types of microspheres.

Figure 1P:
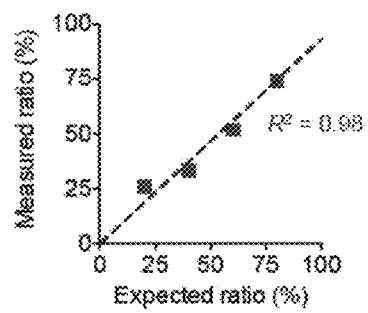
FIG. 1P is a graph showing a graph of a measured ratio of Ag coated to control beads in a mixture, as a function of the expected ratio.

To validate quantitative analysis based on this threshold value, mixtures of Ag-coated microspheres and control microspheres were prepared with known mixing ratios, and the number of Ag-coated microspheres in the mixtures was counted using the above threshold value for identification. The measured ratios for Ag-coated microspheres agreed well with the expected ratios. FIG. 1P is a plot of the measured ratio as a function of the expected ratio. The $R^2$ value for the correlation line in the figure is 0.98.

As a further diagnostic, the mean intensities of the microsphere mixtures were measured. In general, as the proportion of Ag-coated microspheres in the mixture increase, the mean intensity of the microspheres decreases due to the lower transmittance of Ag-coated microspheres. The measured mean intensities showed an excellent correlation with the mixing ratios ($R^2$>0.99), demonstrating that accurate quantitative measurements of target sample constituents can be made using the methods and systems disclosed herein. Further, both analog (e.g., measurement of mean transmittance) and digital (e.g., counting the numbers of Ag-coated and non-Ag-coated microspheres) measurements can be made using the same systems. Digital analysis in particular can be useful for detecting small quantities of target sample constituents, such as rare cells. The use of Ag-coated microspheres allows target sample constituents to be detected at concentrations ranging from millimolar (mM) to femtomolar (fM).

In addition to Ag, other materials can also be used to coat microspheres to impart contrast in diffraction-based images. Materials suitable for such purposes include, for example, metallic, metal-oxide, semiconductor, and/or semiconductor-oxide materials such as Au, Pt, Al, Cu, Ni, Fe, Cd, Se, Ge, Pd, Sn, iron oxide, $TiO_2$, $Al_2O_3$, and $SiO_2$, and combinations of such materials.

Figure 1Q:
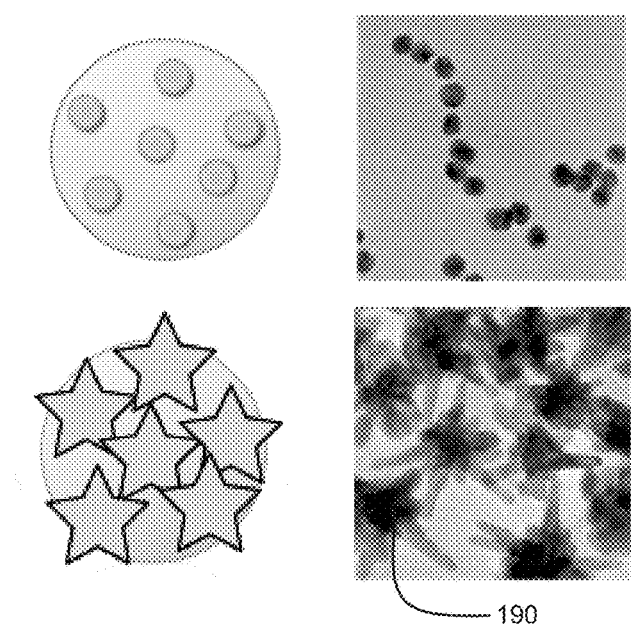
FIG. 1Q is a sequence of images showing Au nanostars and Au nanospheres.

In some embodiments, Au nanoparticles with shapes that are different from the approximately spherical Au nanoparticles disclosed above can be used. For example, FIG. 1Q shows an example of star-shaped gold nanoparticles 190 (Au nanostars) that are conjugated to target sample constituents bound to microspheres. Ag shells are formed over the Au nanostars 190, and the microspheres are imaged and the images analyzed to detect target sample constituents.

Au nanostars 190 are typically grown in a seed-mediated growth procedure from spherical Au nanoparticles. As an example, Au nanoparticles of diameter approximately 12 nm can be injected into a solution of $HAuCl_4$. $AgNO_3$ and ascorbic acid can then be added sequentially to grow the nanostars. The size and number of spikes can be controlled by varying reagent concentrations and reaction time. Methods for synthesizing the Au nanostars are described further in Sau et al., *Small* 7: 2188-2194 (2011), the entire contents of which are incorporated by reference herein. To maintain colloidal stability in physiological solution, stabilizers such as PEG-thiol and/or 2-(perfluoroalkyl)ethanol can be coated on the surface of the AU nanostars.

Figure 1R:
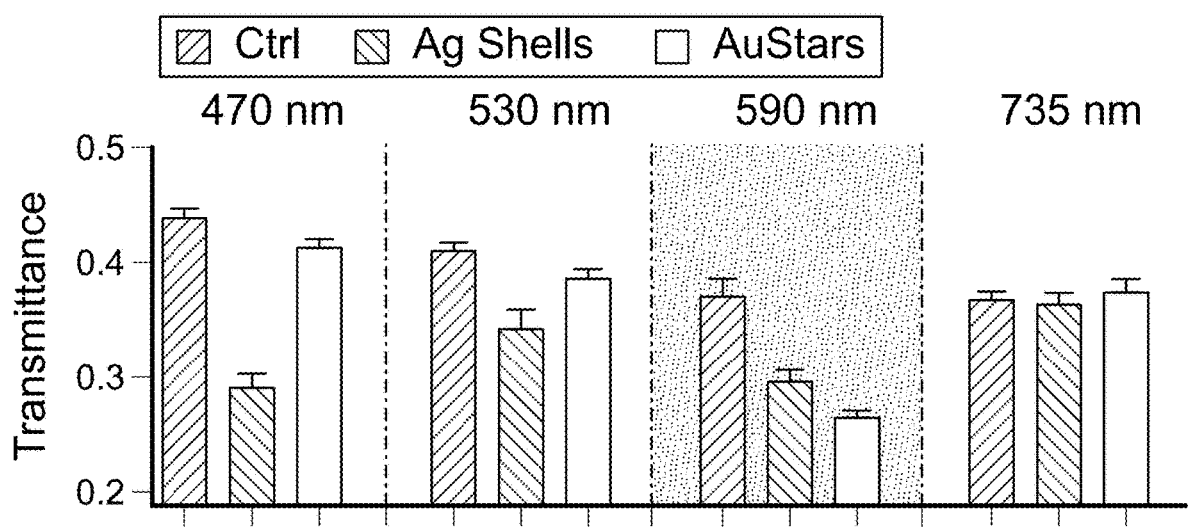
FIG. 1R is a graph showing reconstructed transmittance as a function of illumination wavelength for control beads, beads coated with Ag nanospheres, and beads coated with Au nanostars.

The spiky shape of the Au nanostars can lead to contrast enhancement among labeled and non-labeled sample constituents. FIG. 1R is a plot of transmittance for nanoparticles of various types at several different wavelengths. At each wavelength, transmittance values for control (left bar), Ag-shell-coated (middle bar), and Ag-nanostar-coated (right bar) nanoparticles are shown. As shown in FIG. 1R, maximum absorbance for Au nanostars bound to sample constituent elements is red-shifted to 590 nm, relative to spherical Au nanoparticles.

Figure 1S:
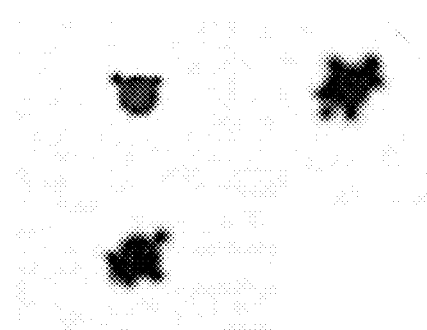
FIG. 1S is an image showing microspheres of different sizes bound to sample cells.

In certain embodiments, detection of sample constituents can be aided by using different sizes of microspheres to bind to the constituents. FIG. 1S is an image showing microspheres of different sizes (diameters 20 microns and 6 microns) bound to sample cells. The systems and methods disclosed herein can detect and distinguish among microspheres of various sizes for purposes of sample analysis.

Diffraction-Based Diagnostic Systems

Figure 2:
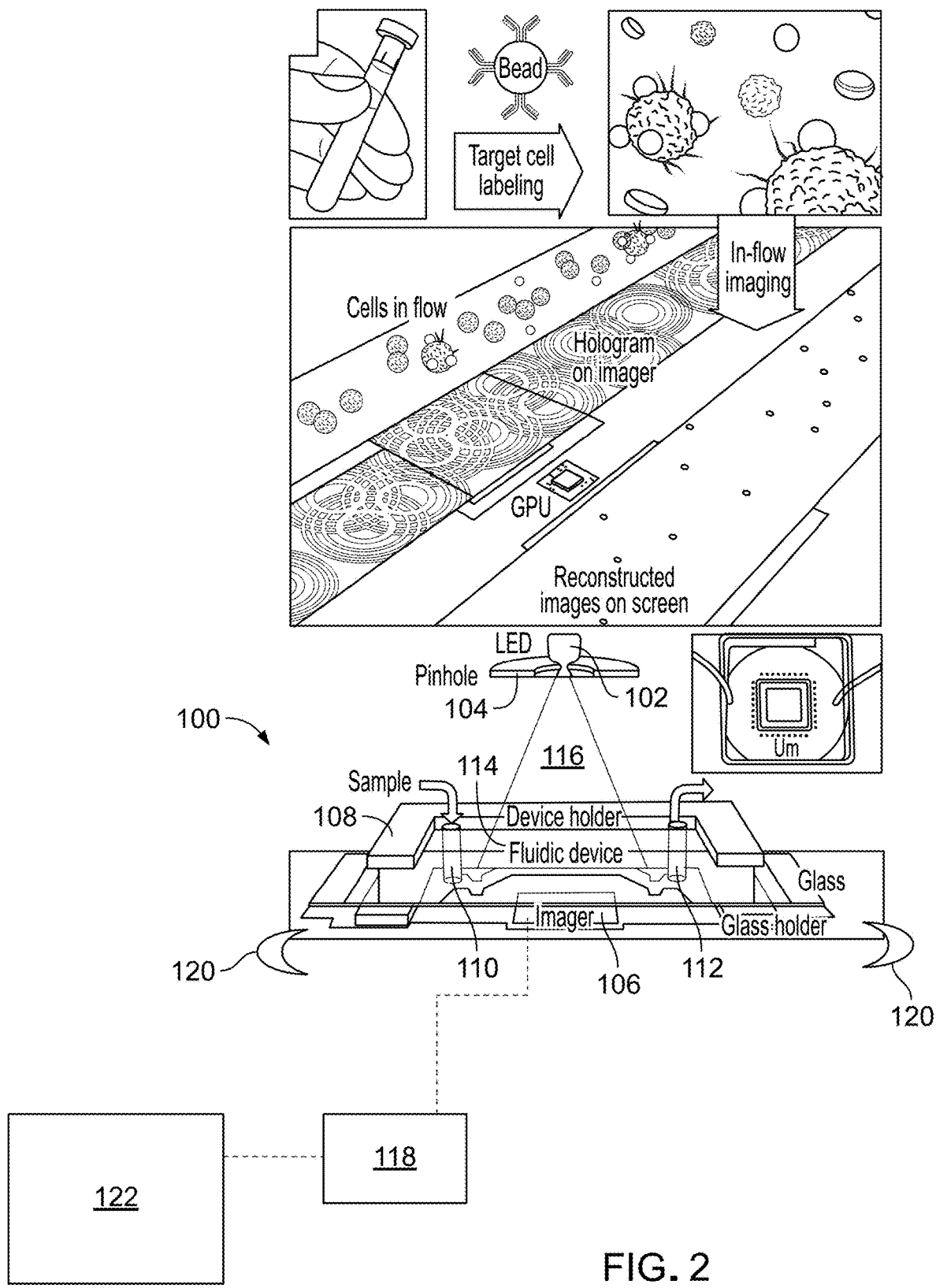
FIG. 2 is a schematic diagram of a system for imaging of samples.

After a sample is labeled, it is introduced into a detection system for analysis. FIG. 2 is a schematic diagram of a system 100. System 100 includes a light source 102 (e.g., including one or more light emitting diodes (LEDs), a spatial aperture 104, a detector 106, and a sample holder 108. In the embodiment shown in FIG. 2, sample holder 108 includes a flow path 114 with an inlet port 110 and an outlet port 112.

During operation, light source 102 generates light which is directed through spatial aperture 104, e.g., a pinhole. Aperture 104 is sized to spatially filter the light from light source 102 to generate at least partially coherent illumination light 116. Illumination light 116 is incident on a sample positioned in or on sample holder 108. Light emerging from the sample is detected by detector 106 as a diffraction pattern of the sample. The pattern is transmitted to electronic processor 118 for analysis.

Although light source 102 is described above as including one more LEDs, more generally, light source 102 can be formed from a variety of elements. In some embodiments, for example, light source 102 can include one or more fluorescent elements and/or one or more diode-based elements and/or one or more incandescent elements. Light generated by source 102 is typically narrowband light, with a full width at half maximum spectral bandwidth of less than 25 nm (e.g., less than 20 nm, less than 15 nm, less than 10 nm, less than 5 nm). Light source 102 can generate pulsed light or continuous-wave light. In some embodiments, for example, light source 102 can be or include an LED, e.g., a model M420L2 LED (available from Thorlabs, Inc.) with an emission wavelength of 420 nm and a line width of 12 nm.

Aperture 104 can be formed from a variety of materials, including various metals such as stainless steel, aluminum, nickel, and alloys. To generate partially coherent light from the light generated by source 102, aperture 104 is typically positioned within 1 mm or less (e.g., 0.9 mm or less, 0.8 mm or less, 0.7 mm or less, 0.5 mm or less, 0.3 mm or less) of source 102. Further, the diameter of aperture 104 is typically selected as desired to condition the light generated by source 102. In some embodiments, for example, the diameter of aperture 104 is 150 µm or less (e.g., 125 µm or less, 100 µm or less, 75 µm or less, 50 µm or less). In some embodiments, for example, the aperture can be a 100 µm diameter pinhole (e.g., model P1005, available from Thorlabs, Inc.)

Detector 106 can be formed from a variety of different light detecting elements. In some embodiments, for example, detector 106 includes a complementary metal oxide semiconductor (CMOS)-based sensor. In certain embodiments, detector 106 includes a charge-coupled device-based sensor (i.e., a CCD chip). For example, detector 106 can include a CMOS monochromatic image sensor (Aptina Imaging, MT9P031).

In certain embodiments, electronic processor 118 is integrated within system 100. For example, system 100 can include a housing (not shown in FIG. 2) and electronic processor 118 can be positioned within the housing along with the other components of system 100. Electronic processor is connected to detector 106 (and, optionally, to light source 102) via one or more connection lines within the housing.

In some embodiments, electronic processor 118 is not integrated within system 100. For example, electronic processor 118 can be located in a computing device that is remotely located relative to system 100. After detector 106 captures sample images, the images can be transmitted wirelessly (e.g., using a wireless transceiver, not shown in FIG. 2) to electronic processor 118 for analysis using a variety of transmission protocols and/or networks, such as mobile telephone or cellular-equipped tablet networks, local wireless (WiFi) networks, and the internet.

In certain embodiments, system 100 can be in the form of a device that does not itself include a detector or camera, but is designed and configured to physically interface with a standalone camera, e.g., a digital camera, or to interface with the camera of a mobile telephone or tablet, and to use the camera, e.g., the mobile telephone's camera or the tablet's camera, as detector 106. In the description that follows, the systems will be described with reference to attachment to a mobile telephone. However, it should be understood that the systems disclosed herein are also capable of attachment to tablets and other portable imaging and/or computing devices.

In FIG. 2, system 100 includes attachment mechanisms 120 that allow system 100 to be attached to a mobile telephone. Cameras located on computers can also be used. In these embodiments, detector 106 in FIG. 2 corresponds to the telephone's front- or rear-mounted camera. Electronic processor 118 can correspond to a processor of the mobile telephone (e.g., a graphics processing unit of the mobile telephone). Alternatively, electronic processor 118, as described above, can be located in a computing device that is remote from system 100, and diffraction image information captured by the mobile telephone's or tablet's camera can be transmitted to electronic processor 118 wirelessly, e.g., using a wireless transceiver in the mobile telephone or tablet to transmit the information over a mobile telephone network or a WiFi network.

Figure 3A:
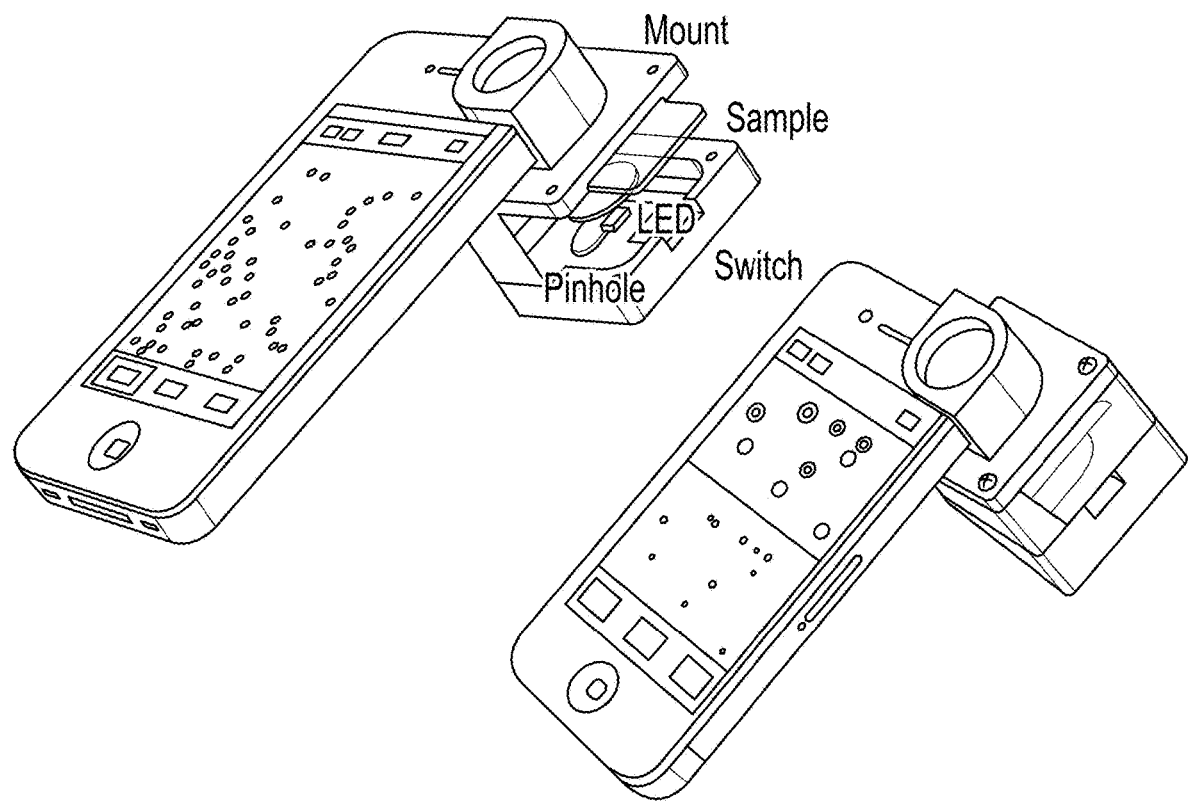
FIG. 3A is a schematic diagram showing a system for imaging that attaches to a mobile telephone or other handheld device.

FIG. 3A shows a perspective view of an embodiment of system 100 that is configured to physically interface with a mobile phone. The left-hand diagram in FIG. 3A shows a schematic cut-away view of system 100, while the right-hand diagram shows a schematic view with a housing that encloses the components of system 100.

Figure 3B:
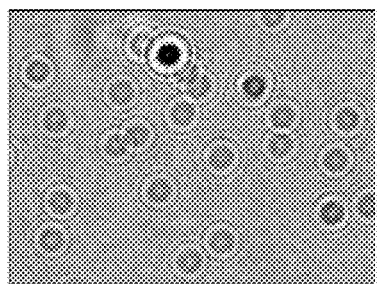
FIG. 3B is a diffraction pattern of cells obtained using the system of FIG. 3A.
Figure 3C:
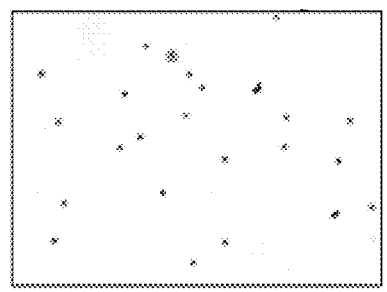
FIG. 3C is a reconstructed image of cells obtained from the image of FIG. 3B.

Returning to FIG. 2, a display 122 is connected to electronic processor 118. Information (e.g., image information) can be transmitted from processor 118 to display 122 wirelessly and/or over a wired connection. In some embodiments, display 122 is integrated into system 100 (e.g., mounted within or on a housing of system 100) and is a display screen that includes, for example, a liquid crystal array or a LED-based array. In certain embodiments, display 122 corresponds to a screen of a mobile telephone or a screen on a digital camera or computer monitor. When system 100 is configured to physically attach to a mobile telephone, system 100 can use the display of the mobile telephone to display image information, as will be described in further detail below. For example, FIG. 3B shows a diffraction pattern of a sample obtained with the system shown in FIG. 3A and displayed on a mobile telephone's display screen. FIG. 3C shows a reconstructed image obtained from analysis of a sample image, as will be discussed in further detail below, and displayed on the display screen of the mobile telephone shown in FIG. 3A.

Embodiments in which system 100 physically attaches to a mobile telephone or tablet can be particularly advantageous, as they take advantage of the nearly ubiquitous presence of mobile communication devices to permit highly sensitive diagnostic imaging measurements in a wide variety of clinical and point-of-care settings. An application running on the mobile telephone or tablet can perform the image capture and information transmission functions described herein, either automatically or in response to instructions from a system operator.

In FIG. 2, the sample holder 108 includes a flow path or chamber 114 with an inlet 110 and an outlet 112. During sample imaging, the sample flows through flow path 114 and detector 106 captures one or more images (e.g., diffraction patterns) of the sample. As will be discussed in greater detail later, each of the images is processed to yield a reconstructed image of the sample in real time or near real-time. Because many types of target sample constituents (such as certain types of cancer cells) are relatively rare in blood samples, directing the sample to flow through sample holder 108 during imaging and analysis permits a larger volume of sample to be analyzed than would otherwise be possible, so that detection of rare sample constituents is more likely to occur. As used herein, a "real time" reconstruction of a diffraction pattern to generate a reconstructed object image of the sample is one that is performed in 0.1 second or less.

Additional aspects of the microfluidic flow path, and methods for concentrating target constituents in samples, e.g., whole blood samples, for analysis using microfluidic devices, are disclosed, for example, in Chung et al., *Adv. Healthcare Mater.* 1: 432-6 (2012), in Chung et al., *Biomicrofluidics* 7: 54107 (2013), and in PCT Patent Application No. PCT/US2011/053466, filed on Sep. 27, 2011 and published as WO 2012/047653, the entire contents of each of which are incorporated by reference herein.

Figure 3D:
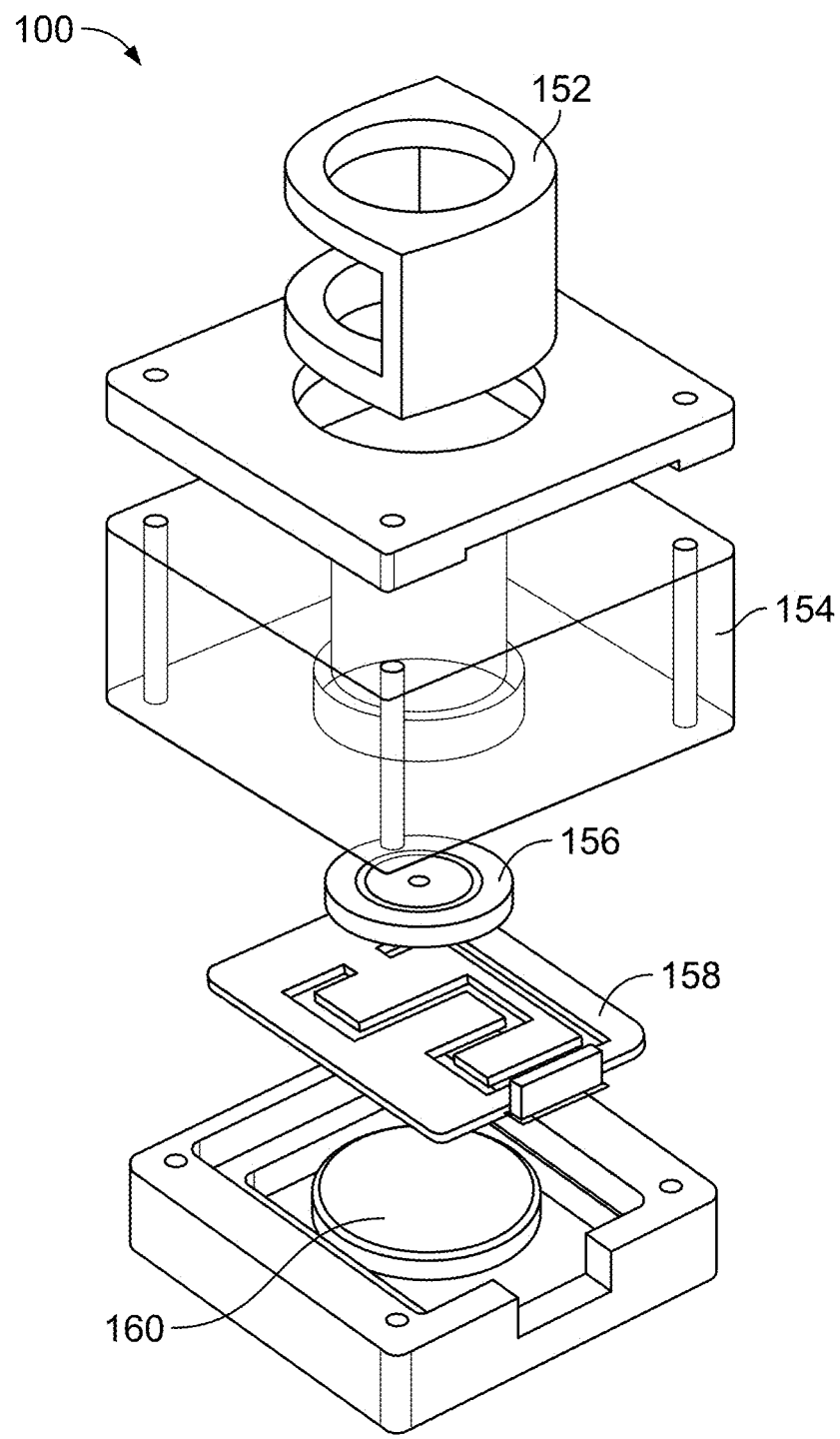
FIG. 3D is a schematic diagram of an exploded view of one example of an imaging system described herein.

In some embodiments, sample holder 108 includes a stage for supporting a microscope slide or a flow channel or flow cell. Samples can be positioned on substrates such as microscope slides and/or between coverslips, which can then be mounted on the stage and analyzed by system 100. FIG. 3D shows a perspective view of an embodiment of system 100 configured for attachment to a mobile telephone. System 100 in FIG. 3D includes an attachment mechanism 152, a stage 154, an aperture 156, a light source 158, and a power source 160.

Light source 158 and aperture 156 function in a manner as described above in connection with FIG. 2. Power source 160, which can be a battery for example, provides operating power to light source 158 for the generation of illumination light. Attachment mechanism 152 functions to connect system 100 to a mobile telephone. As shown in FIG. 3D, attachment mechanism 152 includes two circular apertures positioned at opposite ends of the mechanism. Attachment mechanism 152 slides over an edge of a mobile telephone such that the telephone's camera is aligned with the centers of the circular apertures. In this way, illumination light generated by light source 158 passes through the sample, and light transmitted through the sample is detected by the telephone's camera.

Figure 3E:
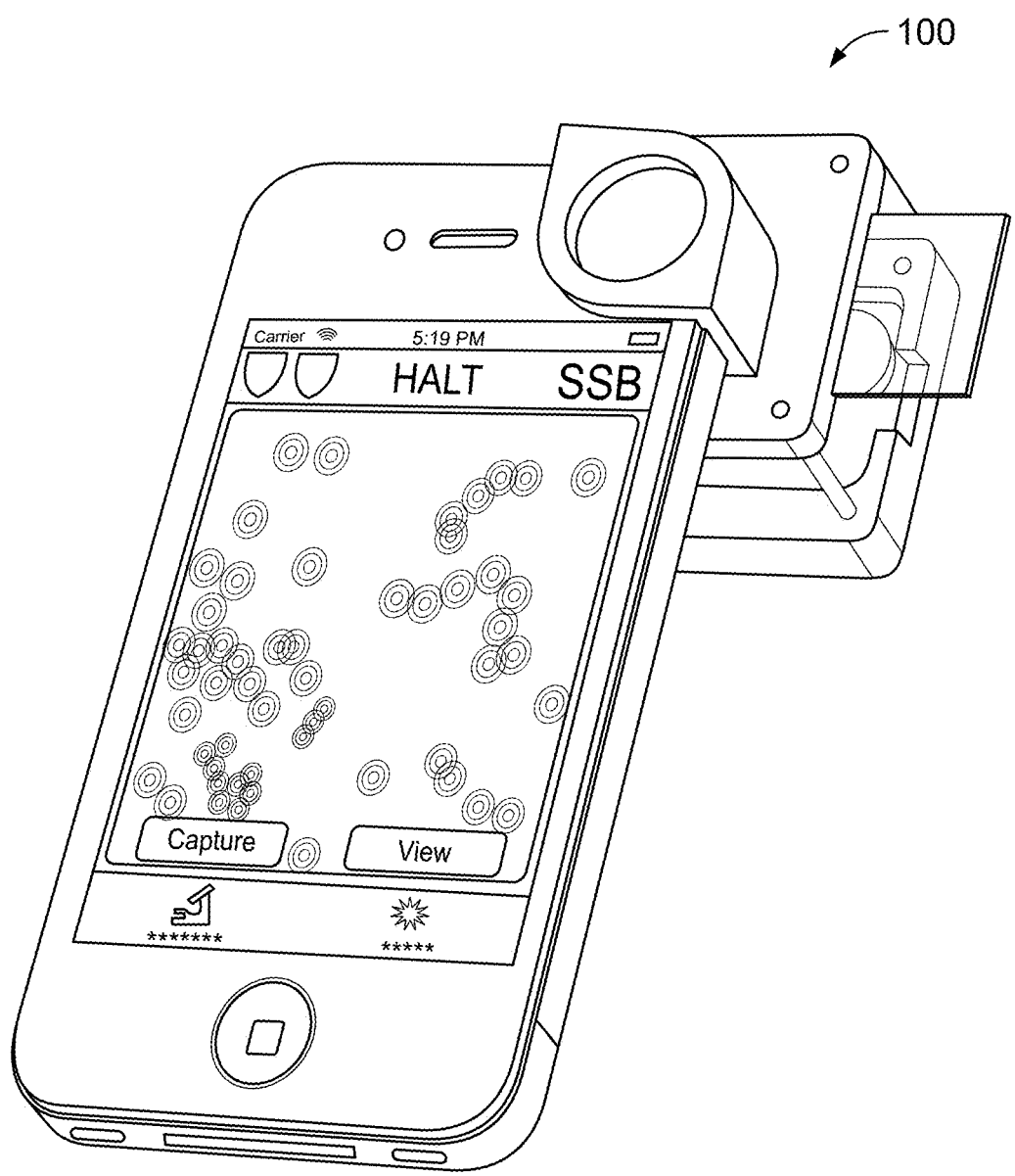
FIG. 3E is a schematic diagram of an imaging system as described herein attached to a mobile telephone as used with a microscope slide on which a sample to be analyzed is deposited.

Stage 154 includes upper and lower portions in FIG. 3D, which together define a slot internal to the stage. The slot is dimensioned to admit a substrate bearing a sample, e.g., a microscope slide or cover slip. Stage 154 also includes an axial opening aligned with the apertures in attachment mechanism 152 and aperture 156. The substrate is inserted into the slot such that the sample is aligned with the apertures in attachment mechanism 152. Illumination light generated by light source 158 can thus be incident on the sample, and the portion of the illumination light that is not absorbed (e.g., the transmitted light) is detected by the mobile telephone's camera. FIG. 3E shows a perspective view of system 100 from FIG. 3D attached to a mobile phone, with a sample-bearing substrate inserted into stage 154.

As explained above, a variety of different processing techniques can be used to analyze sample images. In some embodiments, images obtained by the mobile telephone or tablet can be processed on-board using the device's internal computing hardware. In certain embodiments, images obtained can be transmitted to a remote computing device such as a server (e.g., a cloud-based server), which analyzes the images and transmits analysis results to the mobile telephone or tablet. Images and analysis results can be transmitted and received across a variety of different networks, including cellular networks, WiFi networks, Bluetooth® networks, and the internet.

Figure 3F:
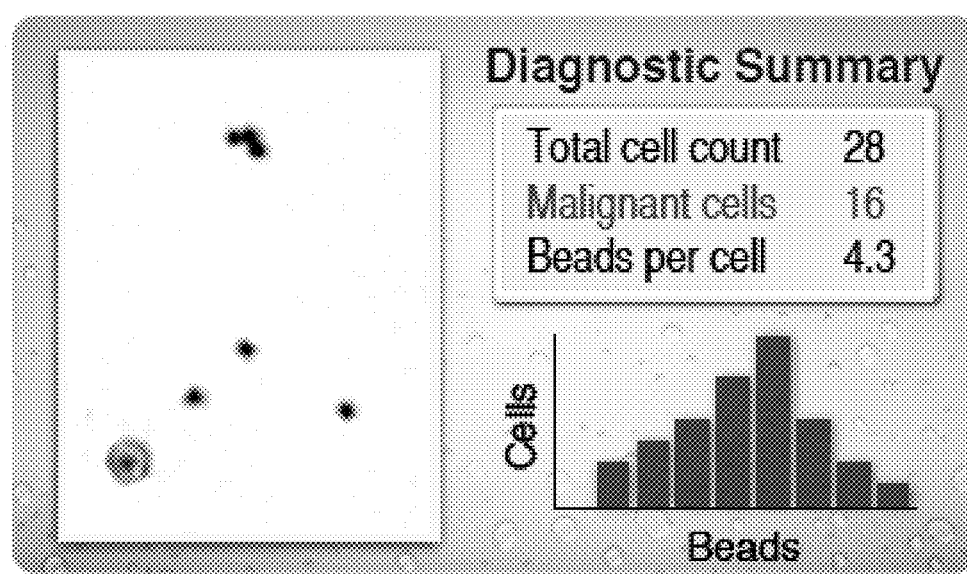
FIG. 3F is a schematic image of a display of a mobile device to which the imaging system is attached showing a reconstructed image and a diagnostic summary.

Analysis results can then be displayed using, e.g., the display screen of the mobile telephone or other hand-held device. In general, any of the information obtained from the analysis of the sample images can be displayed. FIG. 3F is a schematic diagram showing one embodiment of an information display on a mobile telephone. In FIG. 3F, the mobile telephone displays a reconstructed sample image, numerical information about cell counts, and a histogram showing the distribution of beads per sample cell.

Digital Processing of Diffraction Patterns

This section discusses, by way of example, the processing of diffraction patterns by applying digital reconstruction techniques to obtain the amplitude and phase information of objects. However, the techniques discussed are merely examples, and it should be understood that the methods disclosed herein can include obtaining different types of images for purposes of identifying and quantifying sample constituents. For example, as alternatives (or in addition) to diffraction patterns, other types of images, such as phase-contrast images, fluorescence images, phosphorescence images, birefringence images, and other image types in which labeled sample constituents are distinguishable from non-labeled constituents can be used.

Returning to the example of diffraction patterns, compared to conventional microscope imaging, a major limitation of diffraction pattern imaging is that it often involves heavy post-processing to reconstruct object images. As the resolution of the image detector improves, the size of the image files obtained also increases, resulting in long calculation times for image reconstruction. Although multi-core central processing units (CPUs) are available in the market, their calculation efficiency for large-size images is limited and hence, an intrinsic delay of a few seconds to minutes exists when reconstructing an object image from its diffraction pattern. It is therefore highly desirable to achieve rapid processing for real-time imaging (as in conventional microscopy), while preserving the large field of view of diffraction imaging systems.

To achieve real-time or near real-time reconstruction of the diffraction patterns, a graphical processing unit (GPU) can be utilized to perform the analysis. The multi-core structure of a GPU permits numerical reconstruction algorithms to execute much more rapidly than they otherwise would on conventional electronic processors. Once reconstructed, the sample images are then analyzed to locate cells to which microbeads are conjugated; the conjugated microbeads permit rare cells to be distinguished from the other cells in the sample with high specificity and selectivity.

A graphical processing unit (GPU) includes thousands of smaller cores, more optimized for massively parallel threads than CPUs. The GPU can unload heavy calculations from the CPU while the CPU runs the other serial processing, i.e., data transfer between the image detector and CPU. Once a diffraction pattern is transferred to the GPU, it reconstructs an object image through an iterative reconstruction process, called a phase-retrieval algorithm. In particular, in the systems and methods disclosed herein, the CPU transfers diffraction patterns to the GPU and the GPU performs iterative image processing to obtain a reconstructed image. The reconstructed image is then analyzed to detect beads and cells by scanning a representative library image of a bead over the reconstructed image, as will be discussed later. As an example, for a 16 bit, 1024×1024 image (approximately ~1.5 megabytes), it takes about 260 sec for reconstruction and counting using an i3 multi-core CPU processor. When a GPU is used, however, the calculation time is significantly reduced to 0.09 s or less (e.g., 0.08 s or less, 0.07 s or less, 0.06 or less, 0.05 or less) for the same size of image. This rapid processing rate of faster than 10 frames per second enables real-time imaging as well as cell detection for large field-of-view images and continuous analysis of diffraction patterns while the sample is flowing.

Figure 4A:
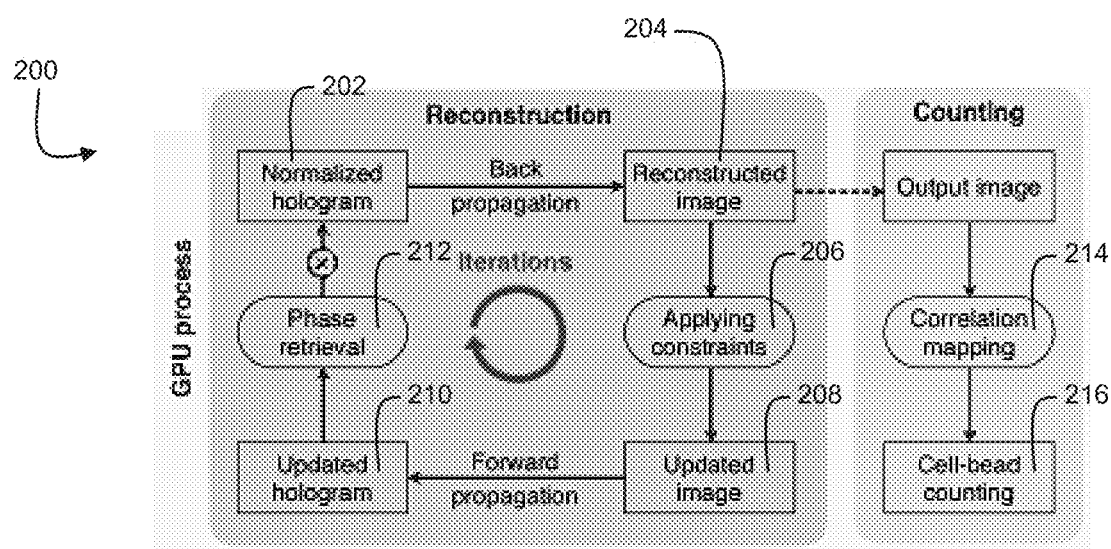
FIG. 4A is a schematic diagram of a flow chart showing a series of steps for analyzing diffraction patterns to identify labeled cells.

FIG. 4A is a flow chart 200 that shows a series of steps for processing diffraction patterns of the sample obtained by system 100. Each pattern obtained by system 100 is processed in turn by electronic processor 118. As discussed above, in some embodiments, electronic processor 118 is a graphical processing unit. In certain embodiments, electronic processor 118 is a portion of a generalized processor that is dedicated to graphical processing.

In a first step 202 of flow chart 200, an acquired diffraction pattern of a sample is normalized against a reference image obtained using detector 106 with no sample in or on sample holder 108. Normalization is performed by dividing each pixel intensity value of the sample diffraction image by the corresponding pixel intensity value of the reference image. This process reduces intensity variations in the diffraction pattern that are due to a non-uniform distribution of illumination light after the illumination light passes through aperture 104.

Next, in step 204, the normalized diffraction pattern is back-propagated according to the distance between detector 106 and each of the objects in the diffraction pattern. The intensity patterns observed in the measured images follow the diffraction theorem, which predicts the propagation of light by the objects. For example, if the propagation distance from an object to an image plane (e.g., the plane of detector 106) is known, the diffraction patterns observed in the image plane can be predicted using the diffraction theorem. Thus, in step 204, back-propagation involves back tracing the shape of original objects (i.e., cells in the reconstructed sample image) from the diffraction pattern. After back-propagation, each pixel value in the reconstructed image represents the light transmittance.

Back-propagation in step 204 corresponds to the transfer of the normalized diffraction pattern from an imaging plane, in which the image is recorded by detector 106, to an object plane, in which the original object(s) (i.e., sample constituents) are located. The transfer is performed by convolving the normalized diffraction pattern with a transfer function from a Rayleigh-Sommerfeld formula. Based on the convolution theorem, the convolution of the diffraction pattern with the transfer function can be calculated by an inverse Fourier transform of the product of the individual Fourier transforms of diffraction pattern and the transfer function. Performing the convolution via Fourier transformation typically results in increased calculation speed, especially when a graphical processing unit (GPU) is used for the calculation.

In step 206, constraints are applied to the back-propagated reconstructed image. The reconstructed image obtained in step 204 includes not only the original object image, but also a ghost image of the diffraction pattern, called a twin image, surrounding the original object. To reduce or eliminate the ghost image, constraints are applied to confine the area of the original object (called object support), thereby removing the ghost image residing outside of the object support area. To define the object support, for each pixel, an intensity variation value is calculated from the intensity values of surrounding pixels. The object support is defined by the intensity variation value, which is a maximum at the object boundary. The diffraction pattern can also be upsampled by a factor of 2-4 times, depending on the size of images, to define the object support. Upsampling permits the object support to be defined more tightly and have images look smoother, without adversely affecting the resolution of the image.

In addition to applying this boundary constraint for the objects in the reconstructed image, step 206 analyzes the reconstructed image to locate pixels with light transmittance (i.e., the modulus of intensity) values larger than unity, and forces them to be unity. Since a normalized diffraction pattern is used as an input image, the transmittance of complex objects can be obtained from the intensity of the reconstructed image. For some pixels, however, the transmittance values become larger than unity due to the superimposition of twin images at the pixel. Forcing the transmittance at these pixels to be unity eliminates this condition. In step 208, an updated reconstructed image is calculated based on the constraints applied in step 206.

Next, in step 210, an updated diffraction pattern is generated by forward-propagating the updated reconstructed image obtained in step 208, in a process that is opposite to the back-propagation step 204. Updated phase information is retrieved from the updated diffraction pattern in step 212. This phase information is not available in the original diffraction pattern, and can only be retrieved from the digital reconstruction process. Steps 202, 204, 206, 208, 210, and 212 are repeated until the reconstructed image converges (i.e., differences in the reconstructed image in successive iterations are smaller than an established threshold value). In some embodiments, a limit on the number of iterations can also be established (for example, the process shown in flow chart 200 can be halted after between 10 and 30 iterations).

Figure 4B:
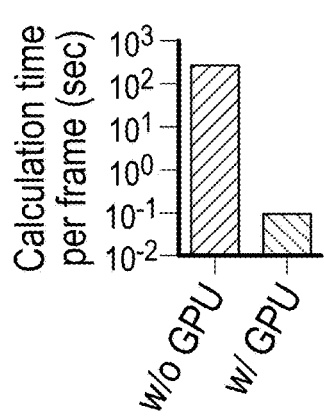
FIG. 4B is a graph comparing diffraction pattern processing times using a graphical processing unit and a standard central processing unit.

FIG. 4B shows the increased rate at which digital processing can occur by performing the processing steps shown in FIG. 4A in a graphical processing unit (GPU). For a single 16 bit, 1024×1024 image, the calculation time reduces from 264 s to 0.09 s when the GPU is used for the reconstruction and counting analysis.

Figure 4C:
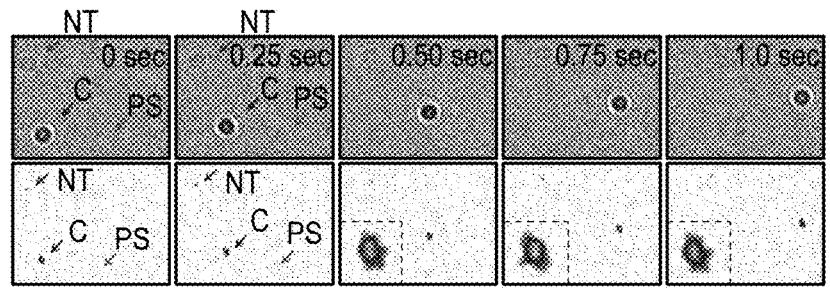
FIG. 4C is a time sequence of images illustrating movement of a labeled cell through a flow channel.

FIG. 4C shows individual frames of a diffraction-pattern movie recorded at 4 frames per second for moving sample constituents (cells) at a flow rate of 0.4 mL/hr. The captured frames show bead-labeled cancer cells ("C"), non-targeted cells ("NT") and polystyrene beads used for labeling ("PS") flowing from left to right. The insets are magnified images of the bead-labeled cancer cell ("C") showing its rotational motion in the flow stream.

Figure 5:
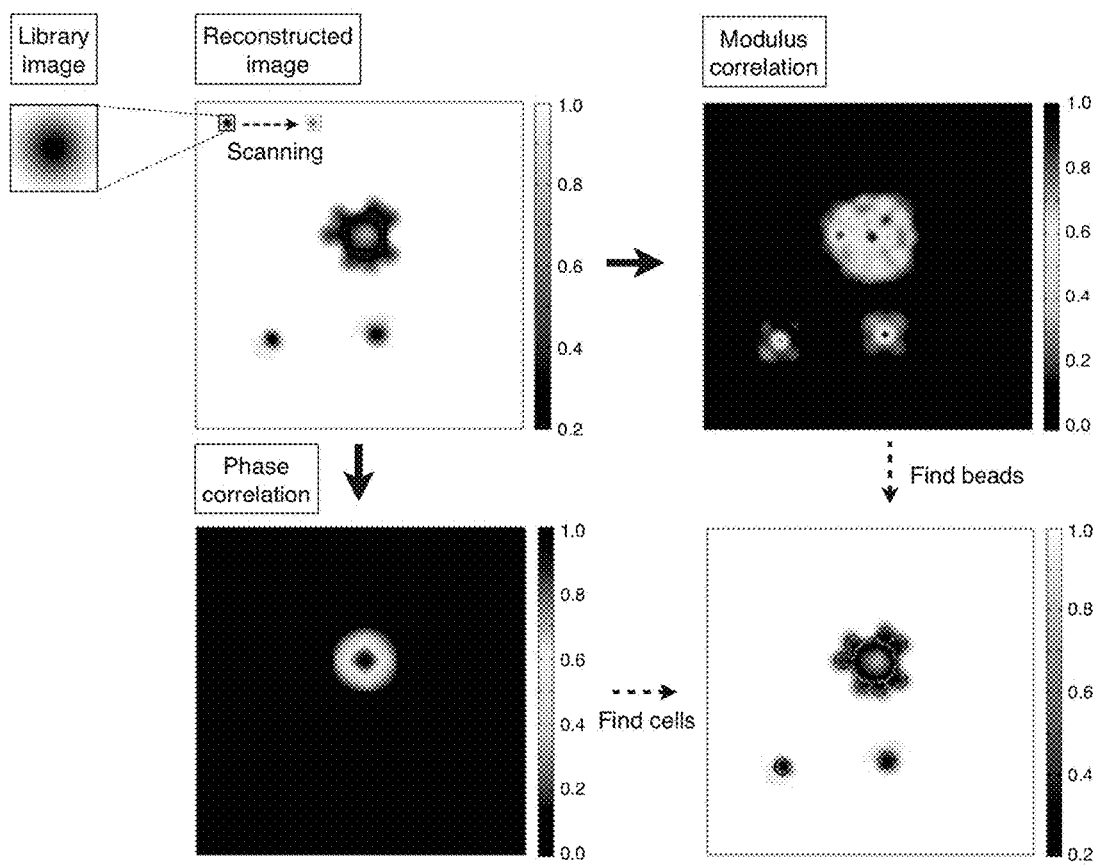
FIG. 5 is a schematic diagram showing modulus and phase images that are used to identify cells and beads.

To detect beads in the reconstructed images, candidate objects in the reconstructed images are compared to a library image of a bead. FIG. 5 shows a series of images that demonstrate this process. In a first step, a library image of bead is obtained by averaging several selected representative bead images obtained from an image of a pure bead solution.

Once obtained, the library image is scanned over an entire reconstructed image, as shown in the upper left panel of FIG. 5. A sub-image window of the reconstructed image having the same size as the library image is compared with the library image. Both modulus and phase values of the sub-image window and library image are compared pixel-by-pixel, respectively, and the similarities of modulus and phase are represented as normalized correlation coefficients values (i.e., step 214 in FIG. 4A). Correlations between the modulus values of the sub-image window and the library image are shown in the upper right panel of FIG. 5. Correlations between the phase values of the sub-image window and the library image are shown in the lower left panel of FIG. 5.

The amplitude correlation map in the upper right panel of FIG. 5 shows the similarity scores of each object to the library bead. An object with higher correlation scores is more likely to be the library bead used for targeting particular sample constituents. Thus, to detect beads (i.e., step 216 in FIG. 4A), pixels at local maxima in modulus correlation above a threshold value are considered first. At each such pixel satisfying this criterion, the phase correlation value and absolute phase values are also considered because the phase values of beads are typically much smaller than those of cells and certain other sample constituents.

To find cells or other sample constituents, local maxima in phase correlation values above a threshold value are considered. This is based on an assumption that the sample constituents (for example, cellular organelles including leucocytes and cancer cells in blood samples) have complex values of transmittance, resulting in a larger contrast in phase than polymer beads. Thus, in phase correlation maps, transparent sample constituents (e.g., cells) will have large phase contrast relative to the image background.

Using these criteria, beads and sample constituents (e.g., cells) are distinguished from the image background and from one another, without using any library images of biological samples. After they have been distinguished, they can be counted and/or displayed (e.g., using display 122) using a variety of different modalities. For example, in some embodiments such as in FIG. 5, identified beads and sample constituents (e.g., cells) are marked by circles.

In some embodiments, both labeled and non-labeled sample constituents are displayed together. For example, labeled constituents can be displayed in a first color, and non-labeled constituents can be displayed in a second color different from the first color. A time sequence of images can be displayed on display 122, allowing a system operator to monitor the flow of particular labeled sample constituents (e.g., cells) through system 100 as a function of time. Such a sequence of images is shown, for example, in FIG. 4C.

Other types of information can also be displayed using display 122. In some embodiments, for example, one or more histograms showing the frequency of different types of beads conjugated to sample constituents, and/or the frequency of different numbers of beads conjugated to sample constituents, can be displayed in addition to, or instead of, reconstructed image information. An example of such a histogram is shown in FIG. 10C.

In the foregoing examples, diffraction images are analyzed to obtain information about samples. More generally, however, the systems and methods disclosed herein can be used with a variety of imaging techniques and modalities. For example, diffraction-based images such as holographic images can be used and analyzed in a similar manner.

As another example, techniques such as phase-contrast microscopy yield images with both amplitude (e.g., transmittance or reflectance) and phase information. The methods and systems disclosed herein can be used with phase-contrast images for sample analysis.

In addition, the methods and systems disclosed herein can be used for other applications that generate optical amplitude and phase information. For example, the methods and systems can be used to analyze scene information captured with head-mounted cameras (e.g., on visual prosthetic devices) and to derive information about the scene from extracted amplitude and phase information. Analysis results can be delivered in real-time or near-real-time, as discussed above.

Applications (a) Detection of Cells

The methods and systems disclosed herein can be used to detect a wide variety of cells, including different types of rare cells. For example, as discussed above, circulating tumor cells (CTCs) can be selectively labeled, identified, and counted using the methods herein. As another example, fetal cells in maternal blood can be selectively identified and counted and/or isolated for further analysis, e.g., genetic analysis for determining genetic disorders. Certain white blood cells, for example CD4+ lymphocytes, can be identified and counted, e.g., for obtaining a diagnosis of Human immunodeficiency virus infection/acquired immunodeficiency syndrome (HIV/AIDS). Other white blood cell counts can be used in known diagnostic assays. For example, a neutrophil count can be used to diagnose neutropenia. More generally, cells for which specific antigen-antibody pairs are available to selectively conjugate microbeads to the cells can be identified and counted. Different types of beads (e.g., cocktails of different antigen-specific beads) can also be used to label different types of cells. The number of labeled cells, the number of beads conjugated to each cell, and the types of beads conjugated to each cell, provide important diagnostic information for clinicians, e.g., for the diagnosis of various disorders.

By way of example, to label specific target cells in blood samples with microbeads, 0.6 mL spiked blood samples were mixed with 12 mL BD Phosflow Lyse/Fix buffer (1×) for 15 min at 37° C. The cells were resuspended in 1×PBS containing 2% serum and 1% BSA (PBS+). Each aliquoted sample contained $5\times10^5$ white blood cells and either a) $5\times10^4$ orb) $5\times10^3$ A431 cancer cells. Each sample in 0.2 mL PBS+ solution was sequentially labeled with biotinylated anti-EGFR (2 µg/mL, 8 biotin molecules/antibody) and streptavidin-coated polystyrene particles (0.5 mg, 6.7 µm diameter, Spherotech), each for 10 min at room temperature.

In the following examples, system 100 was used to obtain diffraction patterns of various samples. A custom-made copper bottom plate along with a plastic top plate was used to place cover slips and/or a microfluidic flow-cell at a distance of 1.5 mm from the detector surface. The detector integration time was adjusted to have mean intensity placed at the middle of intensity range and the typical integration time was around 40 ms. For static measurements, a 10 cell/bead-containing solution was dropped on a 22×22 mm cover glass (Fisher scientific, 12-544-10) and covered by the same cover glass. A reference image was taken without samples with an integration time showing the same mean intensity. For continuous flow measurements, a flow cell made of polydimethylsiloxane (PDMS) was prepared by a mixture of 10:1 base and curing agents. The PDMS flow cell was permanently bonded on a cover glass through oxygen plasma treatment and the inner surface of the flow cell was pre-coated by 1% bovine serum albumin (BSA, Pierce) solution before injecting sample solutions.

Figure 6:
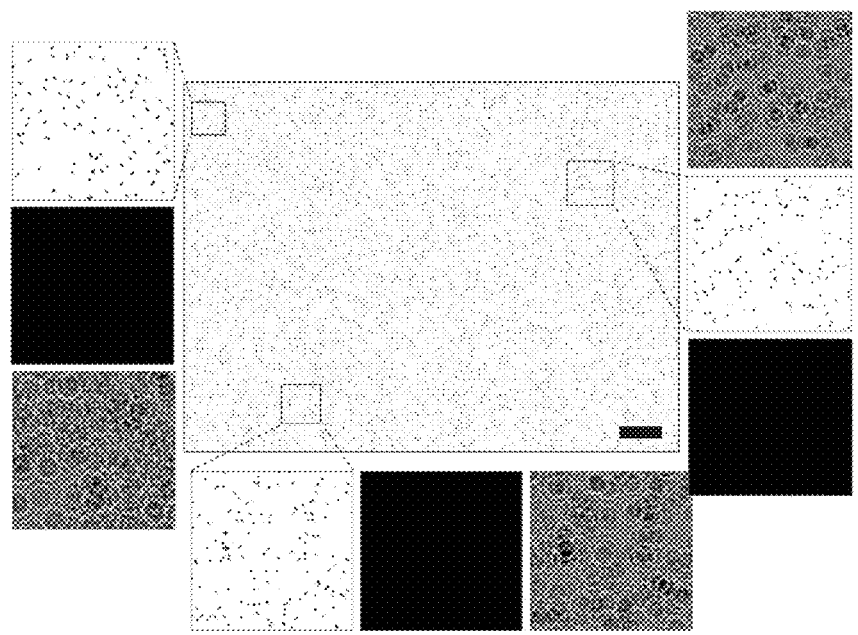
FIG. 6 is a set of images showing reconstructed amplitude, phase, and raw diffraction patterns of three different regions of a sample that includes only polystyrene immunobeads.

FIG. 6 shows reconstructed amplitude, phase, and raw diffraction patterns of three different regions of a sample that included only polystyrene immunobeads. The size and concentration of the immunobeads were 7 µm and $3\times10^7$ beads/mL, respectively. The scale bar represents 500 µm.

Figure 7:
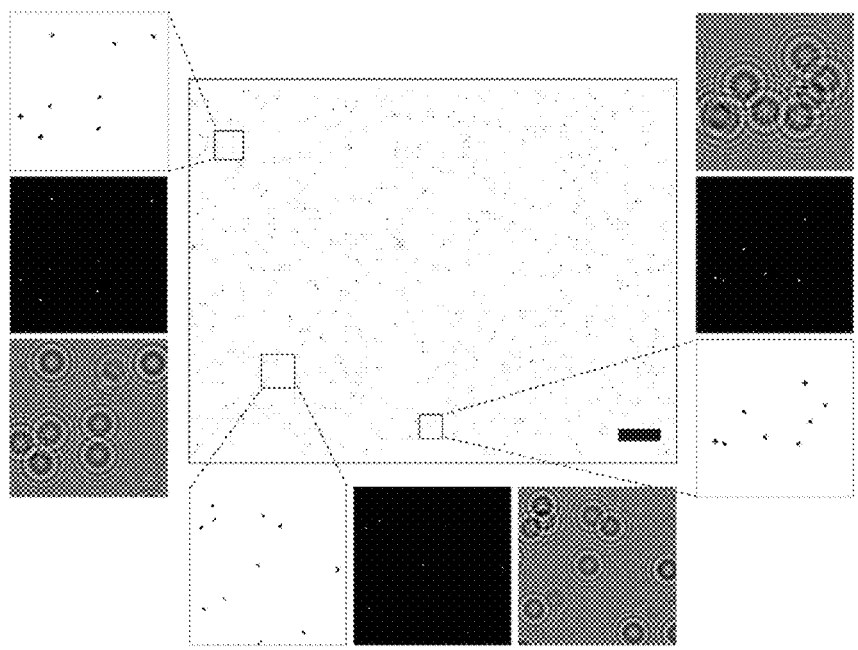
FIG. 7 is a set of images showing reconstructed amplitude, phase, and raw diffraction patterns of three different regions of a sample that includes only leukocytes.

FIG. 7 shows reconstructed amplitude, phase, and raw diffraction patterns of three different regions of a sample that included only leukocytes. The concentration of the leukocytes obtained from a normal human blood is about $5\times10^6$ cells/mL. The scale bar represents 500 µm.

Figure 8:
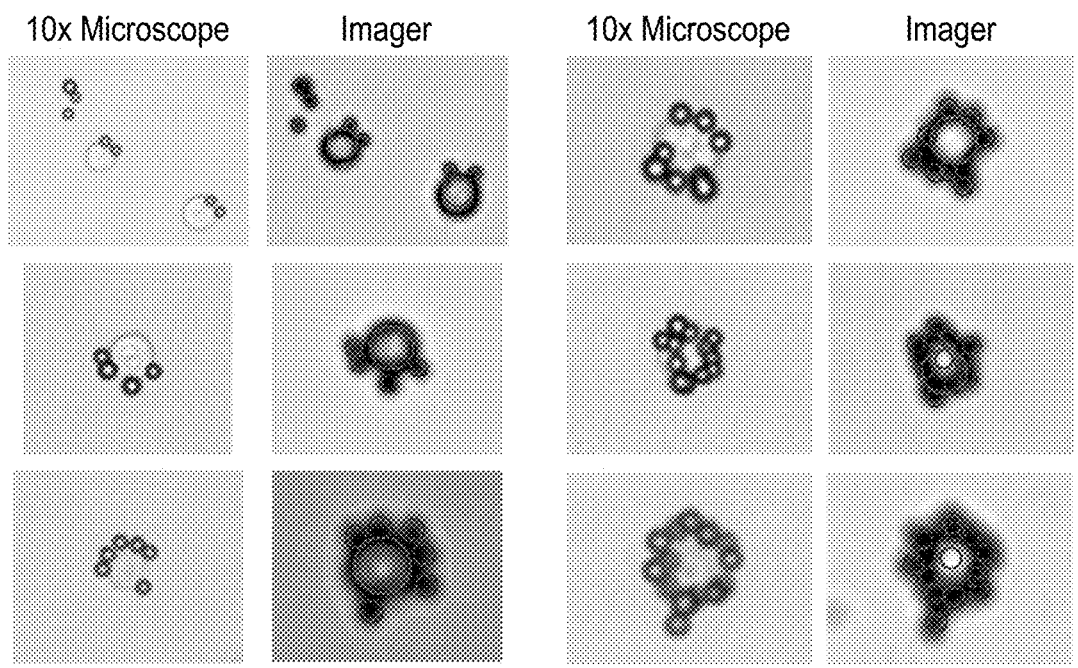
FIG. 8 is a set of images showing a comparison between microscope images of cancer cells labeled with different numbers of immunobeads, and images of the same cells obtained with a diffraction-based diagnostic system as described herein.

FIG. 8 shows a comparison between microscope images ("10× Microscope") of cancer cells labeled with different numbers of immunobeads, and diffraction patterns ("Imager") of the same cells obtained with system 100. As is evident from FIG. 8, images obtained using system 100 permit accurate identification and counting of cells and beads.

Figure 9A:
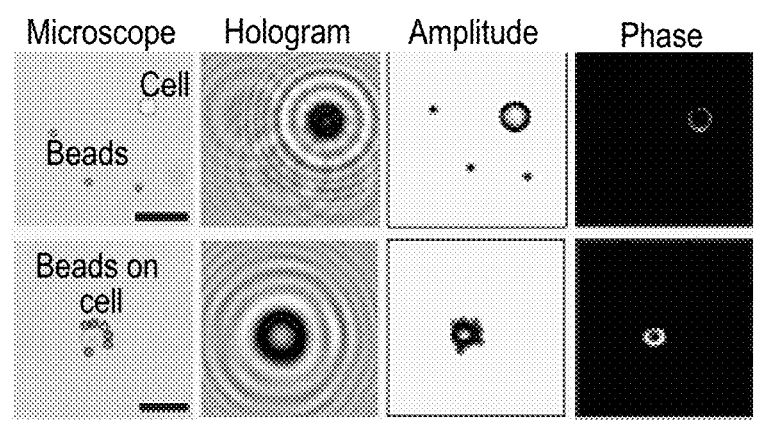
FIG. 9A is a sequence of microscope and corresponding diffraction, amplitude, and phase images of different portions of a sample.

As discussed above, while conventional microscopes use special accessories such as phase-contrast filters to obtain phase information, in diffraction-based imaging, the phase information in addition to amplitude information can be retrieved from a single diffraction pattern. FIG. 9A shows both microscope and diffraction patterns of two different regions of a sample. Both the amplitude and the phase are obtained from each of the single diffraction patterns, which were obtained without using special phase-sensitive detection hardware. While both cells and beads are clearly shown by the amplitude of reconstructed images, only cells are shown in the phase image.

Figure 9B:
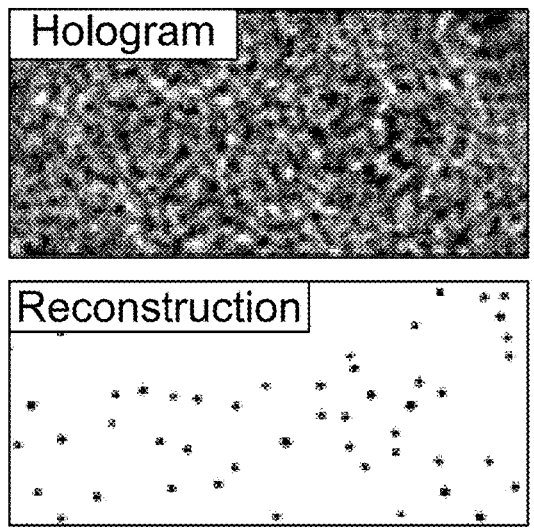
FIG. 9B is a diffraction pattern of a sample and its corresponding reconstructed image.

Phase information is useful for distinguishing transparent specimens, such as cells, from similar sizes of polystyrene beads, especially when the beads are attached to the cells. When cells are mixed with 7 µm polystyrene beads, only cells are clearly visible in the phase images while both cells and beads are visible in the amplitude images. The methods disclosed herein facilitate the identification of both cells and beads using the amplitude images, and identification of cells using phase images. To validate the counting methods disclosed herein, different concentrations of 7 µm polystyrene beads and white blood cells, respectively, were counted. First, diffraction patterns of the different samples were obtained and reconstructed to identify objects (e.g., cells and beads) in the images. FIG. 9B shows an example of such a diffraction pattern, and its corresponding reconstructed image.

Figure 9C:
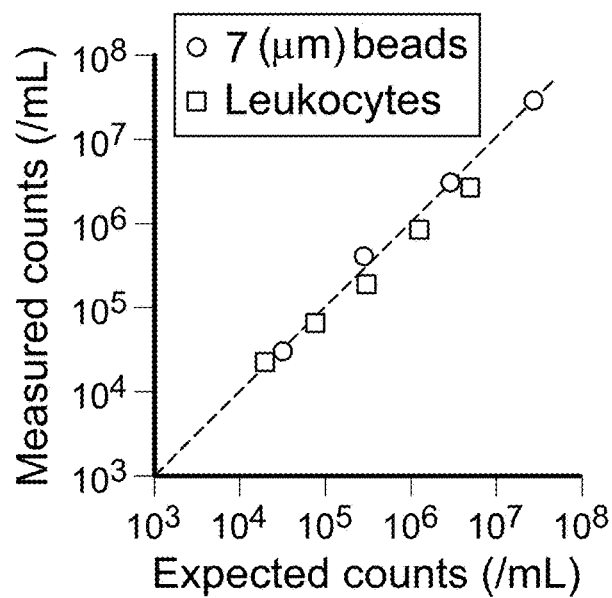
FIG. 9C is a graph showing a correlation between measured counts and expected counts of beads and leukocytes in samples.

Next, beads and cells were identified from the amplitude and phase correlation maps obtained from the image reconstruction process and counted, as disclosed herein. The results of the counting processes are shown in FIG. 9C. Both the stock concentration of beads ($5\times10^7$ beads/mL) used for labeling and the concentration of leukocytes in human blood ($5\times10^6$ cells/mL) were accurately measured using the counting methods disclosed herein, based on expected counts. These results show that additional purification or washing steps are not necessary to remove excessive beads or leukocytes to detect rare cancer cells. As a result, the methods disclosed herein shorten the assay time and also prevent the loss of target cells during such additional steps.

To evaluate the capability of the systems and methods disclosed herein for molecular profiling of cancer cells, a human breast cancer cell line, SK-BR-3, was screened for three different markers: human epidermal growth factor receptor 2 (HER2)/neu, epithelial cell adhesion molecule (EpCAM), and epidermal growth factor receptor (EGFR). The SK-BR-3 cells were first targeted by biotin-conjugated antibodies, which act as a linker to capture streptavidin-coated beads on the cell surface. The number of beads attached to the cells was different depending on the antibody used for labeling: the largest number of beads was found when HER2 was targeted followed by EpCAM and barely detected for EGFR. This indicated that the SK-BR-3 cells over-express HER2 and a moderate amount of EpCAM while EGFR expression is negligible. This finding was confirmed by confocal fluorescence microscopy, in which each antibody was tagged by fluorescent molecules instead of beads.

Figure 10A:
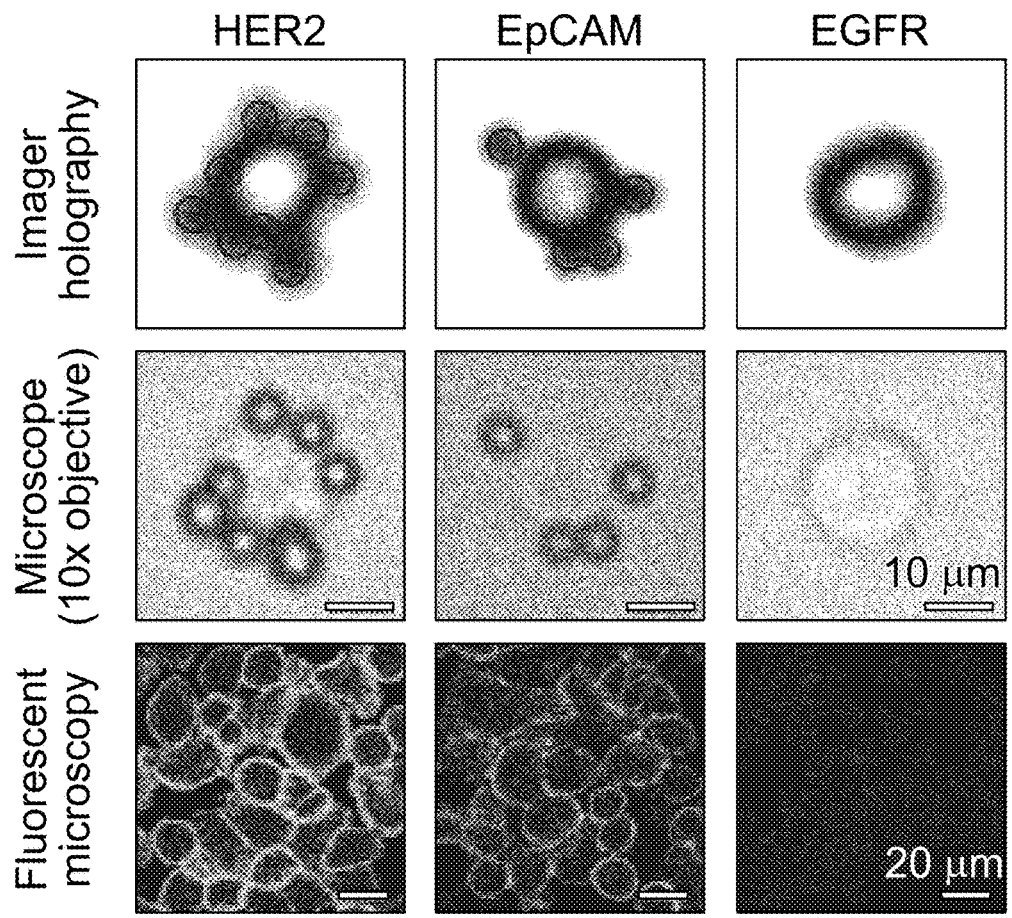
FIG. 10A is a set of diffraction, optical microscope, and fluorescence images of labeled cells.
Figure 10B:
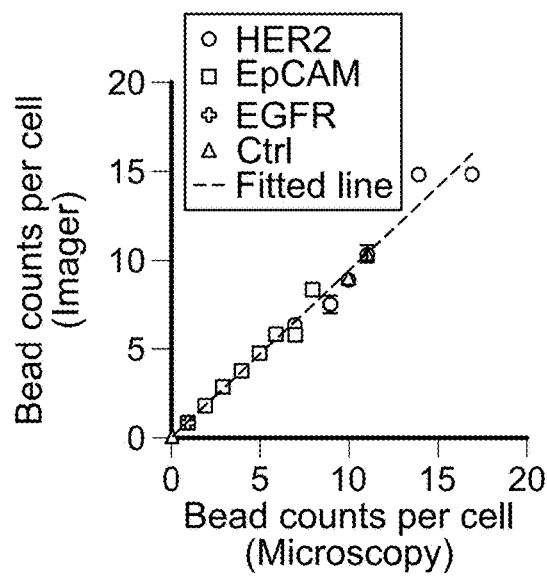
FIG. 10B is a graph showing correlations between bead counts per cell determined from diffraction patterns and from optical microscope images for differently labeled cells.
Figure 10C:
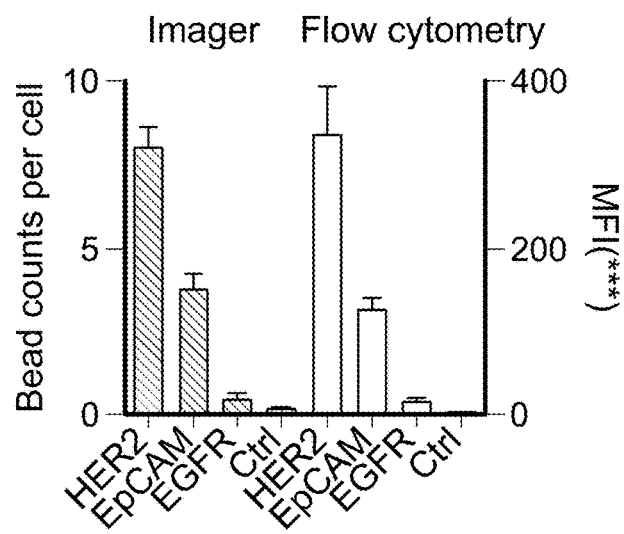
FIG. 10C is a histogram showing bead counts per cell for different microspheres conjugated to cells, as determined from diffraction patterns and from flow cytometry analysis.

FIG. 10A shows reconstructed images of cells obtained using the methods disclosed herein, corresponding optical microscope of the same cells, and fluorescence microscope images of the same cell lines. Bead counts on the cells obtained using the methods disclosed herein show good correlation with bead counts obtained manually from microscope images, up to 17 beads per cell ($R^2>0.97$), as shown in FIG. 10B. Quantitatively, the mean number of beads for each marker linearly correlated with the mean fluorescence intensities measured by flow cytometry, the gold standard used in the clinic for molecular profiling ($R^2>0.98$), as shown in FIG. 10C. When a human epidermoid carcinoma cell line, A431, was tested with the same set of antibodies, EGFR was over-expressed in the A431 cell with a moderate amount of EpCAM, but negligible expression for HER2, as shown in FIG. 8. Overall, the results obtained using the systems and methods disclosed herein show good agreement with results from confocal fluorescence microscopy and flow cytometry analyses.

(b) Cervical Cancer Screening

The global burden of cervical cancer and the disproportionate access to prompt pathology services and emerging cell profiling technologies increase the need for low-cost, portable, and rapid point-of-care (POC) approaches in resource-limited settings. Moreover, emerging genomic data and precursor biology for cervical cancer supports the need to adopt profiling strategies in a manner more accessible to providers and clinical investigators. While conventional and advanced microscopy remain prevalent and important diagnostics tools, their costs (e.g., fluorescence, confocal, and other added features) and complexity challenge reliable and feasible implementation across rural areas and inner cities. The systems disclosed herein represent a viable alternative for diagnostic purposes because of their low cost, simple setup, portability, and notably, high throughput due to superior field-of-view and depth-of-field capabilities.

The methods and systems disclosed herein can readily be applied to the diagnosis of disorders such as high-risk HPV-mediated pre- and frank cervical cancers (HPV=human papilloma virus). To investigate the diagnostic capabilities of the methods and systems for this purpose, twenty women with previous abnormal pap smears at high risk for cervical cancers were subjected to biopsy or loop electrosurgical excision procedure (LEEP). Under an IRB-approved protocol, biopsies were collected from clinically suspicious sites. Samples were incubated with a cocktail of biotinylated antibodies specific to EpCAM and Trop2, followed by incubation with streptavidin-coated microbeads. Aliquots of samples were also analyzed via conventional pathology (gold standard).

Figure 11A:
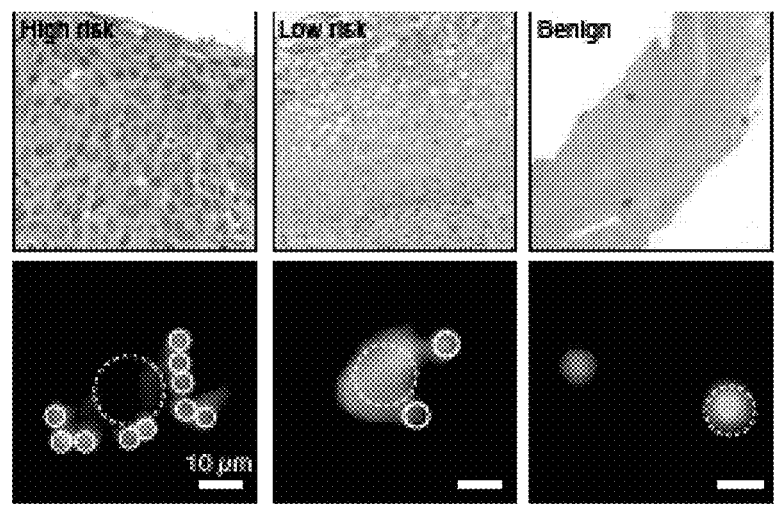
FIG. 11A is a sequence of images showing histology and reconstructed diffraction patterns from high-risk, low-risk, and benign patient samples.

FIG. 11A shows histology and reconstructed diffraction patterns from high-risk (cervical intraepithelial neoplasis/ CIN 2,3), low-risk (CIN 1), and benign patient samples. Samples were targeted with a cocktail of EpCAM, CD44, and Trop-2 antibodies, followed by microbead labeling. The images in FIG. 11A shows that in general, more beads were bound to cells in higher risk patient samples.

FIG. 11B is a graph showing average bead count for each of the patient samples. Determination of average bead count by diffraction pattern analysis achieved high detection accuracy (96%) for high-risk patients, in excellent agreement with conventional pathologic detection. FIG. 11C is a scatter plot showing the distribution of average bead counts for high-risk, low-risk, and benign patient samples. The average bead counts for each category of samples were significantly different, as FIG. 11C demonstrates.

FIG. 11D is a receiver operation characteristic curve for the high-risk vs. low-risk sample groups. Digital diffraction diagnosis on cells achieved high accuracy (95%) in distinguishing high-risk samples.

The foregoing results demonstrate that the methods and systems disclosed herein are readily applied to the identification and quantification of cervical cells of varying cancer-risk levels in samples. The methods and systems rapidly yield accurate diagnostic information that can then be used to treat at-risk patients. The simplicity of the methods and systems ensures that even in resource-limited environments, rapid triage, diagnoses and initiation of treatment are possible.

Emerging genomic data about cervical cancer argue for analyses involving increasing numbers of markers (e.g., more than 5). The systems and methods disclosed herein can be used in multiplexed analyses involving many different markers. As HPV plays a central role in cervical and many other cancers (e.g. head, neck, and anal cancers), the systems and methods can be used for diffraction-based DNA testing of patient samples, as will be described in greater detail below.

To allow for multiplexed sample analyses, microbeads of different sizes (0.5 micron, 1.0 micron, and 1.5 microns) and colors (blue, red, yellow) can be used. This yields a minimum of six simultaneously available "channels" that can be assayed in real time on a cell-by-cell basis in cervical specimens. In some embodiments, microbeads of different optical transparencies can also be used, to yield up to 12 multiplexing channels.

The main markers of interest are EpCAM, Trop2, and CD44, but various other biomarkers (e.g., p16 and Ki-67) can also be analyzed to help identify women at risk for high-grade squamous intraepithelial lesions (HSIL) and cervical cancer.

Specimens can be suspended in about 2 mL of fixation/permeabilization buffer, and subsequently aliquoted into round-bottom plastic tubes. The tubes can then be capped with a nylon-mesh filter for the removal of large tissue debris, and contain the antibody-coated beads in lyophilized form, for durable storage.

(c) Detection of Human Papilloma Virus (HPV)

The new systems and methods can also be used to detect viruses, e.g., human papilloma virus (HPV) in body samples, e.g., blood and cervical smears. HPV is the most common sexually transmitted infection in the United States and comprises various subtypes. Certain subtypes, when not cleared by the body, impart significant risk for cancers of the vulva, vagina, penis, anus, and oropharynx. Immunocompromised states, such as HIV/AIDS, are often the cause for failure to clear HPV infection; hence, co-infections are common in global regions (e.g. Africa) where HIV/AIDS is highly prevalent.

There are various HPV subtypes with unique DNA sequences; at least eighty-five HPV genotypes are well-characterized. Certain subtypes (HPV 16 and 18) are commonly associated with high risk cervical changes leading to invasive cervical cancers. However, there are geographical differences vis-a-vis prevalence patterns and, as such, HPV subtype detection needs may differ. The methods and systems disclosed herein can be used to detect the various HPV subtypes. For example, in the case of HPV 16 and 18, following the diffraction analysis of intact cells, cell lysates are generated to extract DNA, then mixed with HPV specific primers and transported to a PCR chamber.

FIG. 11E is a schematic diagram illustrating the assay method. As described above, in the presence of target DNA, silica microsphere-DNA-Au nanoparticle sandwich arrays are formed. Ag shells are then grown on the surfaces of the Au nanoparticles; the shells form a coating extending across the entire surface of the microsphere.

With Ag shells, the transmittance of the silica microspheres decreases to about 470 nm, which is close to the resonance wavelength of the Ag-coated Au nanoparticles on the silica microspheres. Changes in transmittance are detected. In general, the magnitude of the transmittance change is proportional to the presence and amount of target DNA in the solution. Since both size and transmittance of silica microspheres can be detected, differently sized microspheres can be used for multiplexed DNA assays within the same parent specimen.

By detecting and distinguishing among different types of beads (each corresponding to a different biomarker), HPV detection can be performed by selecting appropriate combinations of biomarkers to target specific DNA sequences. Sequences that can be used for HPV detection are disclosed, for example, in Sun et al., "Whole Genome Sequencing and Evolutionary Analysis of Human Papillomavirus Type 16 in Central China," Plos One 7: e36577 (2012), the entire contents of which are incorporated by reference herein.

Moreover, the methods and systems disclosed herein can also be used to detect other virally-driven illnesses such as, for example, Epstein-Barr virus and Cytomegalovirus.

(d) Diagnosis of Lymphomas and Other Cancers

One of the major health challenges in sub-Saharan Africa is the high prevalence of AIDS-related cancers (the "second wave of AIDS"). Such cancers include very aggressive ones, for example diffuse large B-cell lymphoma and Burkitt's lymphoma. This epidemic has expanded/grown as larger populations gain access to antiretroviral drugs. Patients are now living long enough to develop HIV associated cancers (especially non-Hodgkin lymphoma, cervical cancer, Kaposi sarcoma and head and neck cancers) in part due to their immunosuppression. Cancer survival in the region is low, and only an estimated 5% of patients receive chemotherapy. Most funds are spent on individual systemic treatments for disseminated disease, as many most cancers are not detected at an early stage. Even when care at a major treatment center is sought, there are often delays in work-up and diagnosis due to an overburdened healthcare system and a paucity of specialists trained in oncology subspecialties.

Due to limited resources, a considerable number of these cases evade comprehensive evaluation or are not appropriately classified. Diagnosis and care are further hampered by lack of proper tissue specimens and diagnostic reagents, and lack of access to care in rural settings. Furthermore, the number of cases often outweighs treatment capacities. Although a good proportion of cases are curable even in low and middle income countries (LMICs), windows of therapeutic opportunities are commonly missed. As a result, there is a need for low-cost, fast and accurate detection technology to expedite the diagnosis of aggressive lymphomas (and other prevalent cancers) in this resource limited environment.

The methods and systems disclosed herein can distinguish between multiple different types of beads based on criteria such as bead size and/or absorbance. FIG. 12A is a plot showing measured bead sizes as a function of nominal bead sizes. The correlation coefficient for these measurements, $R^2$, is larger than 0.999. FIG. 12B is a plot showing transmittance values for various different bead types. As is evident from these plots, beads can readily be distinguished based on both criteria. Combining these attributes (e.g., fabricating beads with specific combinations of size and transmission) allows for 9-channel, multiplexed molecular analysis of samples.

Figure 12D:
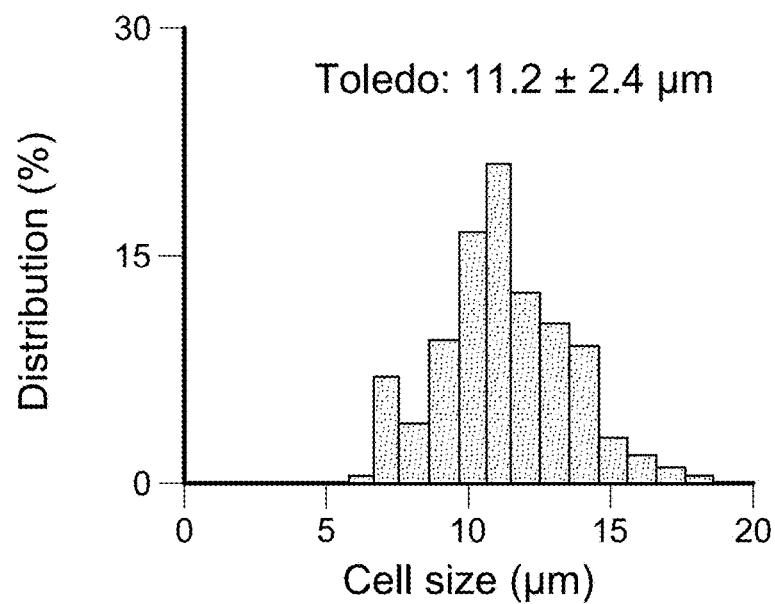
FIG. 12D is a graph showing lymphoma cell size measurements for Toledo cells.

FIG. 12C is a graph showing lymphoma cell size measurements for Daudi cells, and FIG. 12D is a graph showing lymphoma cell size measurements for Toledo cells. The cell size measurements were derived from the digital diffraction analysis. The cell diameters were determined to the 10.0±2.3 microns for Daudi (ATCC CCL-213) cells, and 11.2±2.4 microns for Toledo (ATCC CRL-2631) cells, using 10 micron beads as a calibration standard. These measurements were further confirmed using optical microscopy measurements.

Figure 12E:
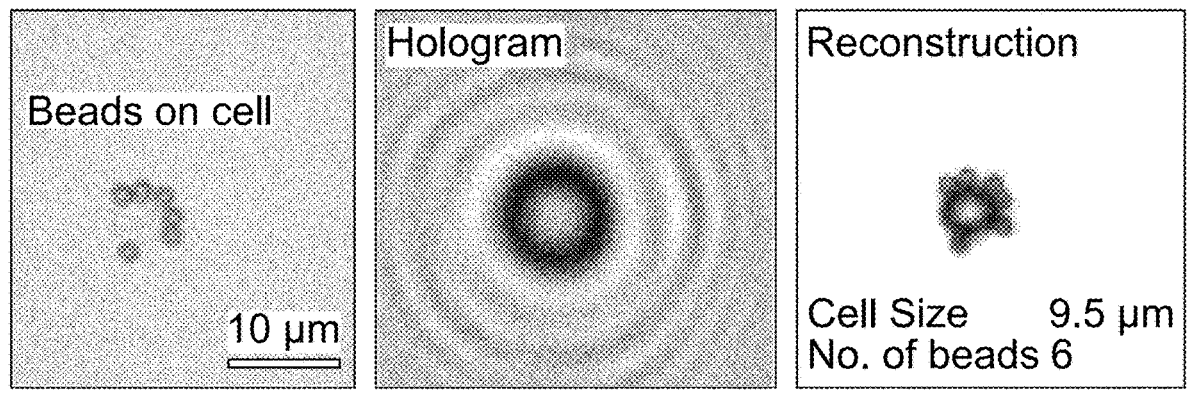
FIG. 12E is a sequence of optical microscope, diffraction, and reconstructed images of a Daudi cell with bound microspheres.

FIG. 12E shows the results of further size measurements for Daudi cells. Daudi cells were incubated with microbeads coated with anti-CD20 antibodies (available from Genentech, San Francisco, Calif.). The left image in FIG. 12E is an optical microscope image of a cell, confirming that bead-binding occurred. A diffraction pattern (center image in FIG. 12E) was obtained. Digital reconstruction yielded the right image in FIG. 12E, and also provided measurements of the size and the number of beads attached to each Daudi cell.

The systems and methods disclosed herein are capable of distinguishing beads that are conjugated with a wide variety of different antibody markers, which is important for purposes of phenotyping the various lymphoma sub-types. In particular, multi-channel analyses can be used in which the systems and methods disclosed herein can distinguish among beads conjugated with CD20, Ki67, CD5, CD10, CD15, CD30, and Pax5. In typical lymphoma diagnostics, at least 5-10 different markers are currently assayed by immunohistochemistry while flow cytometry is usually performed for 16-25 markers.

Given the cost and complexity of detecting up to 25 different markers, a hybrid approach to lymphoma detection, using a simpler algorithm based on two marker sets and cell size, can be employed. This technique can be used to diagnose in five major categories with clinically distinct treatment in LMIC settings: i) Burkitt's lymphoma, ii) diffuse large B-cell lymphoma (DLBCL) or other aggressive non-Hodgkin's lymphomas (NHL), iii) indolent NHL, iv) Hodgkin's lymphoma and v) no lymphoma.

Figure 13:
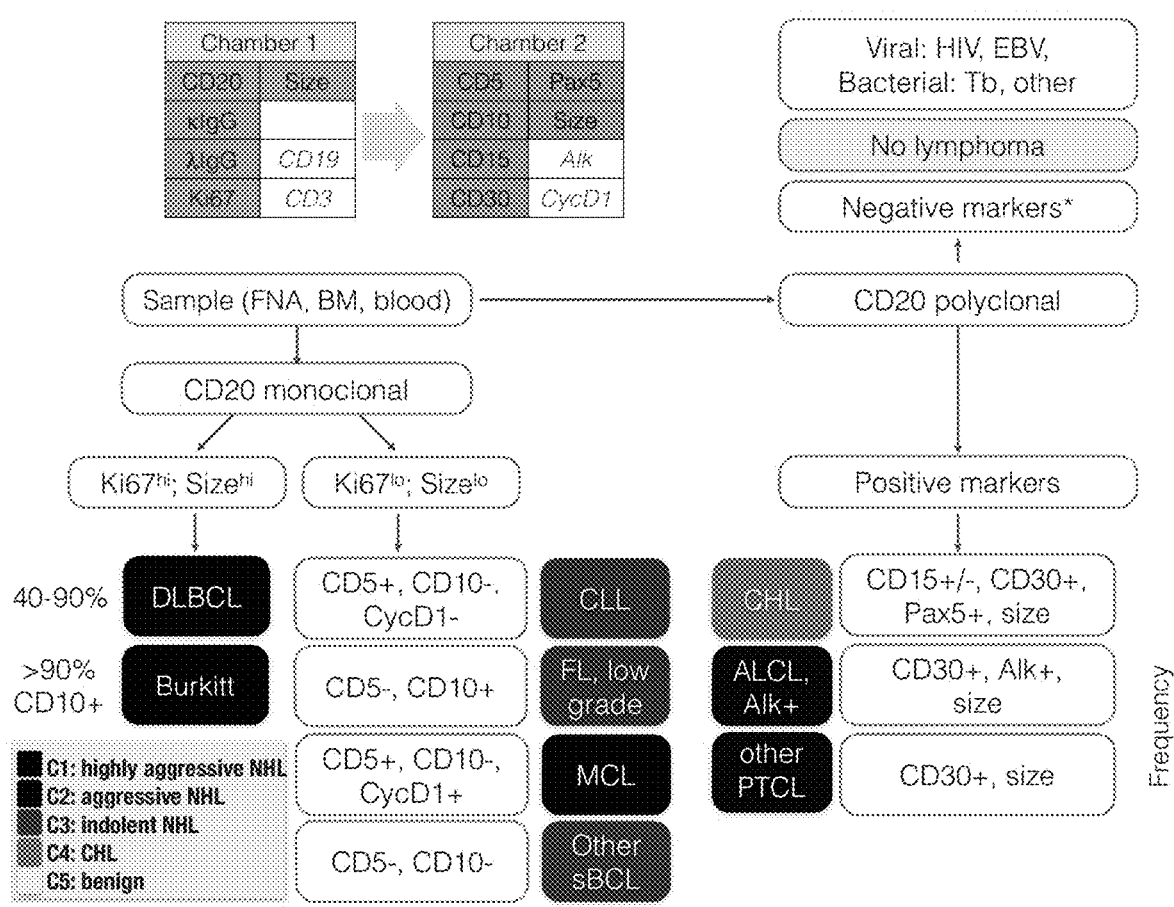
FIG. 13 is a flow chart showing a series of steps for lymphoma detection.

A flow chart illustrating the detection procedure is shown in FIG. 13. Cells corresponding to each of the five major categories can be detected. The following abbreviations are used in FIG. 13.

Burkitt's lymphoma="Burkitt"
Diffuse large B-cell lymphoma="DLBCL"
Chronic leukocytic leukemia="CLL"
Follicular lymphoma="FL"
Mantle cell lymphoma="MCL"
Small B-cell lymphoma="sBCL"
Classical Hodgkin lymphoma="CHL"
Anaplastic large cell lymphoma="ALCL"
Peripheral T-cell lymphoma="PTCL"

Each of the antibodies used in this multiplex detection procedure is encoded by a specific bead size and color, so that each antibody can be distinguished from the others by accurate bead size and color measurements. The sample loading slide includes two chambers, with each chamber used to measure 4-6 different markers, which are as follows.

Chamber 1: CD20, κ, λ, and Ki67
Chamber 2: CD5, CD10, CD15, CD30, Pax5.

Choosing a two-chamber system rather than a single chamber is based on the number of beads that can be attached onto cells; preliminary experiments have shown that 4-6 different beads can be easily fit onto cells and images of such beads are very accurately reconstructed. With this limited set of markers (expandable to some other markers), diagnoses can be made in resource-limited settings.

The algorithm corresponding to the flow chart shown in FIG. 13 can be programmed into the systems disclosed herein, and can easily be altered as desired. The algorithm is derived from literature sources including: Akakin et al., *IEEE Trans. Inf. Technol. Biomed.* 16: 758-769 (2012); Amador-Ortiz et al., *Am. J. Clin. Pathol.* 135: 516-524 (2011); Matasar et al., *Ann. Oncol.* 23: 159-166 (2012); Jaffe, *Hematology Am. Soc. Hematol. Educ. Program*, pp. 523-531 (2009); LaCasce et al., *J. Clin. Oncol.* 26: 5107-5112 (2008); Bogusz et al., *Clin. Cancer Res.* 18: 6122-6135 (2012); and Swerdlow et al., *WHO Guidelines* (WHO Press, 2008, ISBN-139789283224310). The entire contents of each of the foregoing references are incorporated herein by reference.

OTHER EMBODIMENTS

A number of embodiments have been described. Nevertheless, it will be understood that various modifications may be made without departing from the spirit and scope of the disclosure. Accordingly, other embodiments are within the scope of the following claims.

What is claimed is:

1. A diagnostic system comprising:
   a radiation source configured to generate illumination radiation;
   a sample holder configured to support a sample so that the sample is exposed to the illumination radiation;
   a detector configured to obtain one or more diffraction images of the sample, wherein each of the diffraction images comprises information corresponding to optical properties of sample constituents; and
   an electronic processor configured to, for each of the one or more diffraction images:
   (a) for each sample constituent in the diffraction image, identify a corresponding diffraction pattern;
   (b) analyze the diffraction pattern for each sample constituent to obtain spatial amplitude distribution information and spatial phase distribution information corresponding to the sample constituent;
   (c) determine whether each sample constituent comprises a target analyte conjugated to a particle based on at least one of the spatial amplitude distribution information and the spatial phase distribution information corresponding to the constituent; and
   (d) determine an amount of at least one of the conjugated target analytes in the sample based on at least one of the spatial amplitude distribution information and the spatial phase distribution information.

2. The system of claim 1, further comprising an aperture configured to spatially filter the illumination radiation to generate partially coherent illumination radiation that is incident on the sample.

3. The system of claim 1, wherein the electronic processor is configured to:
   (d) generating a reconstructed image of the sample;
   (e) analyzing the reconstructed image of the sample to obtain phase information corresponding to the diffraction of the illumination radiation by the sample;
   (f) analyzing the combined phase information and the diffraction image to obtain an improved reconstructed diffraction image; and
   (g) analyzing the improved reconstructed diffraction image to determine whether each sample constituent comprises a target analyte conjugated to a particle.

4. The system of claim 1, wherein the detector comprises at least one of a charge-coupled device (CCD) and a complementary metal-oxide semiconductor (CMOS) device.

5. The system of claim 1, wherein the detector comprises a camera of a mobile telephone or tablet.

6. The system of claim 5, wherein the electronic processor is a graphical processing unit of the mobile telephone or tablet.

7. The system of claim 1, wherein the sample holder comprises a fluid chamber, an inlet port connected to the fluid chamber, and an outlet port connected to the fluid chamber.

8. The system of claim 1, further comprising a display unit, wherein the electronic processor is configured to display the at least one of the target analytes on the display unit.

9. The system of claim 8, wherein the display unit is a screen of a mobile telephone or tablet.

10. The system of claim 8, wherein the electronic processor is configured to display the one or more target analytes in a first color, and to display other sample constituents in a second color different from the first color.

11. The system of claim 1, wherein the one or more diffraction images comprises multiple diffraction images, and wherein the electronic processor is configured to identify one or more target analytes common to each of the improved reconstructed diffraction images.

12. The system of claim 1, wherein the system is configured to identify target analytes comprising cells.

13. The system of claim 12, wherein the electronic processor is configured to determine, for each cell one or more of the cells, a number of beads bound to the cell.

14. The system of claim 1, wherein the system is configured to identify target analytes comprising viruses.

15. The system of claim 1, wherein the system is configured to identify target analytes comprising nucleic acids.

16. The system of claim 1, wherein the system is configured to identify target analytes comprising bacteria.

17. The system of claim 13, wherein the electronic processor is configured to display a histogram of the number of beads bound to the one or more of the cells.

18. The system of claim 2, wherein each of the reconstructed images corresponds to a portion of the sample flowing through the sample holder.

19. The system of claim 2, wherein the aperture is separated from the radiation source by a distance of 1 mm or less.

20. The system of claim 1, wherein the sample holder comprises a stage configured to support a substrate bearing the sample.

21. A diagnostic system, comprising:
   a radiation source configured to generate illumination radiation;
   a sample holder configured to support a sample so that the sample is exposed to the illumination radiation;
   a detector configured to obtain one or more diffraction images of the sample, wherein each of the diffraction images comprises information corresponding to optical properties of sample constituents; and
   an electronic processor configured to, for each of the one or more diffraction images:
      (a) analyze the diffraction image to obtain amplitude information and phase information corresponding to the sample constituents;
      (b) identify one or more bead-conjugated cells among the sample constituents based on at least one of the amplitude information and the phase information;
      (c) determine, for each bead-conjugated cell, a number of beads conjugated to the cell; and
      (d) determine an amount of at least one of the bead-conjugated cells in the sample based on at least one of the amplitude information and the phase information.

* * * * *

UNITED STATES PATENT AND TRADEMARK OFFICE
CERTIFICATE OF CORRECTION

PATENT NO. : 10,724,948 B2
APPLICATION NO. : 16/025615
DATED : July 28, 2020
INVENTOR(S) : Ralph Weissleder et al.

Page 1 of 1

It is certified that error appears in the above-identified patent and that said Letters Patent is hereby corrected as shown below:

In the Claims

In Column 33, Line 15 (approx.), Claim 13, after "for" delete "each cell"

Signed and Sealed this
Twenty-seventh Day of October, 2020

Andrei Iancu
*Director of the United States Patent and Trademark Office*